(12) United States Patent
Batiste

(10) Patent No.: US 12,303,649 B2
(45) Date of Patent: May 20, 2025

(54) CATHETER CLEARANCE DEVICE AND METHOD OF USE

(71) Applicant: Stanley Batiste, Granite Bay, CA (US)

(72) Inventor: Stanley Batiste, Granite Bay, CA (US)

( * ) Notice: Subject to any disclaimer, the term of this patent is extended or adjusted under 35 U.S.C. 154(b) by 953 days.

(21) Appl. No.: 17/211,741

(22) Filed: Mar. 24, 2021

(65) Prior Publication Data
US 2021/0205578 A1 Jul. 8, 2021

Related U.S. Application Data

(63) Continuation-in-part of application No. 17/141,098, filed on Jan. 4, 2021, now Pat. No. 12,186,465.

(60) Provisional application No. 63/022,358, filed on May 8, 2020, provisional application No. 63/001,166, filed on Mar. 27, 2020, provisional application No. 62/957,088, filed on Jan. 3, 2020.

(51) Int. Cl.
A61M 25/00 (2006.01)
A61M 25/01 (2006.01)
A61M 25/10 (2013.01)
A61M 39/10 (2006.01)

(52) U.S. Cl.
CPC .... *A61M 25/0017* (2013.01); *A61M 25/0108* (2013.01); *A61M 25/10182* (2013.11); *A61M 39/10* (2013.01); *A61M 2025/0019* (2013.01); *A61M 2039/1083* (2013.01)

(58) Field of Classification Search
CPC ...... A61M 25/0017; A61M 2025/0019; A61M 1/285; A61M 25/10182; A61M 5/14228; A61M 5/14232; A61M 5/142; A61M 5/14244
See application file for complete search history.

(56) References Cited

U.S. PATENT DOCUMENTS 3,923,065 A * 12/1975 Nozick .................. A61B 17/22
  604/102.03
3,951,570 A    4/1976 De Biaggi
4,191,181 A    3/1980 Franetzki
(Continued)

FOREIGN PATENT DOCUMENTS

WO    WO 9717102      5/1997
WO    WO 0183019      11/2001
WO    WO-0183019 A1 * 11/2001  ............ A61M 25/10

*Primary Examiner* — Nilay J Shah
(74) *Attorney, Agent, or Firm* — The Powers IP Law Firm

(57) ABSTRACT

A dialysis catheter clearance device comprising a medication delivery device configured to connect to the proximal end of the infusion catheter and selectively output an infusion drug into the infusion catheter. An infusion catheter having the proximal end and an opposing distal end, the proximal end of the infusion catheter connected to the medication delivery device, and the distal end of the infusion catheter having an opening through which medication exits the infusion catheter. An infusion catheter placement device is located at or near the distal tip of the infusion catheter and configured to expand to having an outer dimension that is greater than an inner dimension of the dialysis catheter when the infusion catheter placement device is outside the dialysis catheter and contract to an outer dimension that is less than the inner dimension of the dialysis catheter when the infusion catheter placement device is inside the dialysis catheter.

19 Claims, 24 Drawing Sheets

(56) References Cited

U.S. PATENT DOCUMENTS

| | | | | |
|---|---|---|---|---|
| 4,704,102 | A | * | 11/1987 | Guthery ............ A61M 25/1025 |
| | | | | 604/921 |
| 4,754,752 | A | * | 7/1988 | Ginsburg .............. A61M 25/10 |
| | | | | 604/113 |
| 5,034,004 | A | * | 7/1991 | Crankshaw ......... A61M 5/1456 |
| | | | | D24/111 |
| 5,273,537 | A | * | 12/1993 | Haskvitz ......... A61M 25/10182 |
| | | | | 604/920 |
| 5,484,401 | A | | 1/1996 | Rodriguez |
| 5,620,312 | A | | 4/1997 | Hyman |
| 5,871,467 | A | * | 2/1999 | Reuning ........... A61M 25/0102 |
| | | | | 604/97.02 |
| 2002/0120236 | A1 | * | 8/2002 | Diaz ................ A61M 5/14216 |
| | | | | 417/478 |
| 2004/0097880 | A1 | | 5/2004 | Schur |
| 2006/0173407 | A1 | | 8/2006 | Shaughnessy |
| 2011/0112507 | A1 | * | 5/2011 | Linderman ........... A61M 25/00 |
| | | | | 604/506 |
| 2011/0144620 | A1 | | 6/2011 | Tal |
| 2012/0095537 | A1 | | 4/2012 | Hall |
| 2015/0165110 | A1 | | 6/2015 | Gopalakrishna |
| 2017/0072125 | A1 | | 3/2017 | Wallenas |

\* cited by examiner

CATHETER CLEARANCE DEVICE AND METHOD OF USE

BACKGROUND OF THE INVENTION

1. Field of Invention

The present invention relates to clearance of occluded catheters.

2. Description of Related Art

Patients with end stage renal disease ("ESRD") have lost their normal kidney function, and as a result require dialysis to substitute the function of the kidney cleansing the blood. ESRD affects almost 750,000 people per year in the United States. Hemodialysis requires that large volume blood access and exchange be consistently available to sustain the life of the patient. Medicare coverage is extended to a person of any age who requires either dialysis or transplantation to maintain life. The people who live with ESRD are 1% of the U.S. Medicare population but account for roughly 7% of the Medicare budget. Mortality rates vary depending on the ESRD treatment. After one year of treatment, those on dialysis have a 20-25% mortality rate, with a 5-year survival rate of 35%. Persons who receive transplants have a 3% mortality rate after 5 years. There are two types of dialysis, hemodialysis, and peritoneal dialysis. For purposes of this overview we will primarily be focused on hemodialysis.

Hemodialysis care costs the Medicare system an average of $90,000 per patient annually in the United States, for a total of $28 billion. Typically, a dialysis patient will require 3-4 hours of dialysis three days a week. The challenge with providing hemodialysis is maintaining access to large volumes of blood when a body constantly fights attempts to keep access available by healing closed such access. Currently there are three ways to provide hemodialysis; dialysis catheters, arterial venous fistulas (AVF's) and arterial venous grafts (AVGs). Although used worldwide, catheters are known not to be efficient for long term dialysis. Unfortunately, catheters have very short patency rates and high rates of infection greater than 60% of all dialysis patients use catheters.

Long term catheter patency rates remain low at less than 35% after 1 year and an average patency rate of 80 days. It is the development of a fibrin sheath that determines the long term patency of a catheter. This sheath, initially composed of fibrinogen, albumin, lipoproteins, and coagulation factors, begins to form within 24 hours of insertion. The fibrin sheath attracts platelets and coagulation factors and promotes leukocyte adherence. Over weeks and months, collagen is deposited as smooth muscle cells from the venous vessel wall migrate toward the tip. The rate of these processes varies among patients because of inherited or acquired characteristics. Ultimately, if clotting in excess of the endogenous fibrinolytic system's capacity develops, catheter thrombosis occurs.

There are several ways to restore patency to an existing catheter if it is decided that a new catheter placement at a different site may be delayed. Commonly, a catheter may be exchanged for a new catheter using guidewires as placeholders when the initial catheter is removed. The guidewires are generally advanced using fluoroscopic guidance, the catheter is then liberated from the body tissues and a new catheter is then advanced over the guidewire to the same location as the prior, occluded catheter. This method, although effective, requires patient sedation, access to a surgical or fluoroscopic suite and numerous hospital personnel, including at least one nurse and a physician. The major setback is that the catheter follows in the same tract as the prior catheter and it may be directed into the same fibrin sleeve that has formed.

SUMMARY

Dialysis catheter occlusion is a common problem affecting nearly every hemodialysis patenting who has one. Overall catheter patency rates are low, and catheter use in our system remains high creating increased healthcare costs and significant frustrations for those dialysis patients. A catheter occlusion will generally be discovered at the dialysis center and many times patients will need to go to the hospital for treatment prior to receiving dialysis. Once at the hospital thrombolytic medication can be injected at the entry port or patient can have the surgical or Interventional radiology teams exchange the catheter while sedated. While these methods have shown some success and are currently employed to restore patency, the described invention and method of use creates a much improved means of using the thrombolytic that speeds up lyses times and improved fibrin and clot removal.

The fibrin which can form all along the catheter causes occlusion once the fibrin sheath covers the distal tip. Generally, the inflow port of the catheter will be useable as an injection will displace the fibrin and allow fluid passage out of the catheter. The entry/blood aspiration/draw port however remains non-functional as the fibrin acts as a ball-valve mechanism not allowing blood to flow to the proximal catheter. The inner lumen volume of the dialysis catheter may be upwards of 2 ccs in each port. When thrombolytics are injected they diffuse through the 2 ccs and some of it reaches the tip and goes on to lyse the fibrin. Much of the thrombolytics however remains unused within the length of the catheter not coming into contact with the fibrin at the tip. The described invention is an innovative means of applying the thrombolytics directly at the catheter tip and can be utilized at the patient's bedside without the need for surgical suite or a large medical team.

A non-invasive means of restoring patency to a catheter is that of employing lytic therapy which has proven effective. This is performed by using a syringe to inject a thrombolytic medication such as TPA (Tissue Plasminogen Activator) directly into the proximal port of the catheter and allowed to "soak" in the catheter lumen to dissolve the fibrin sheath at the tip. This may be performed without use of imaging requiring only a nurse to perform. After 1-3 hrs., the catheter is checked for patency by aspiration using a syringe. The invention described relates to thrombolysis of catheter using more directed thrombolytic therapy.

The described innovation utilizes an intraluminal catheter placed with in the lumen of the dialysis catheter to apply directed thrombolysis at the tip where the largest thrombus burden exists. The catheter is created in specific sizes, or in one embodiment—a variable size in order to provide direct infusion. The design allows the user to match the need infusion length with the dialysis catheter size and precisely direct drug infusion at the exact point of need. The application can be performed in a non-surgical setting such as the ED or in the dialysis clinic with the need for only a chest x-ray for placement confirmation.

Although prior art describes the use of catheters for thrombolysis the presented invention creates a means to exploit the standard design of dialysis catheters in order to allow the user to apply the drug in precise location at the patient's bedside or in an outpatient setting such as a dialysis center. To further the utility of the invention means of length and quantity of drug administration are combined as the art combines and infusion module with the measured infusion catheter. The device uses either preloaded medication, or in a second embodiment, the medication is added to the device prior to its use. The invention is used as a disposable, self-contained system which can be matched to the appropriate dialysis catheter taken out of its packaging and either loaded with medication or preloaded then advanced into the patient's catheter, adjusted for medication duration and then turned on. Once the medication has been given, the catheter and system are removed, and the patient can then be dialyzed.

Other systems, methods, features, and advantages of the invention will be or will become apparent to one with skill in the art upon examination of the following figures and detailed description. It is intended that all such additional systems, methods, features, and advantages be included within this description, be within the scope of the invention, and be protected by the accompanying claims. Further, any of the elements and features disclosed herein may be combined in any manner with any of the other elements and features disclosed herein.

DESCRIPTION OF THE DRAWINGS

The components in the figures are not necessarily to scale, emphasis instead being placed upon illustrating the principles of the invention. In the figures, like reference numerals designate corresponding parts throughout the different views

DETAILED DESCRIPTION

Hemodialysis patients require routine large volume blood exchange to survive, and our bodies fight off efforts to allow this access. For many dialysis patients a permanent, indwelling catheter is the means of providing such access. Dialysis catheters have advantages over other methods of access however also have a limited time in which they will stay open and function mainly because of fibrin and clot forming on the tip. This invention and the method of use describe a means to direct a drug, a thrombolytic, directly at the point needed for a specific duration for dialysis catheters which are made in specific standard sizes.

Figure 1:
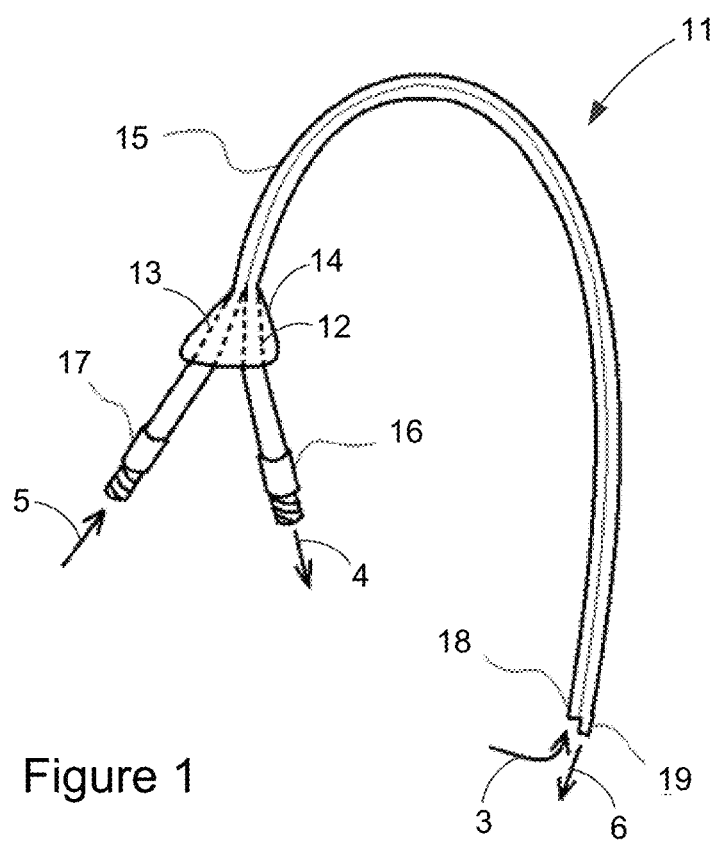
FIG. 1 illustrates a standard tunneled type dialysis catheter.

FIG. 1 illustrates a standard dialysis catheter 11 consisting of an aspiration tube 12, an injection tube 13 held together by a cuff 14 and a catheter 15. The aspiration tube 12 is attached to an aspiration port 16 on one end, and a distal tip on the other end 18. The injection tube 13 is attached to an injection port 17 on one end, and a distal tip on the other end. The arrows 3, 4, 5, 6 represent the direction of the blood flow. Specifically, the patient's blood exits the patient's body by entering 3 the distal tip of the aspiration tube 12, flowing through the aspiration tube 12, and exiting 4 the aspiration port 16 to become filtered. Once filtered, the patient's blood is returned to the patient's body by entering 5 through the injection port 17, flowing through the injection tube 13, and exiting 6 the distal tip of the injection tube 19.

Figure 2:
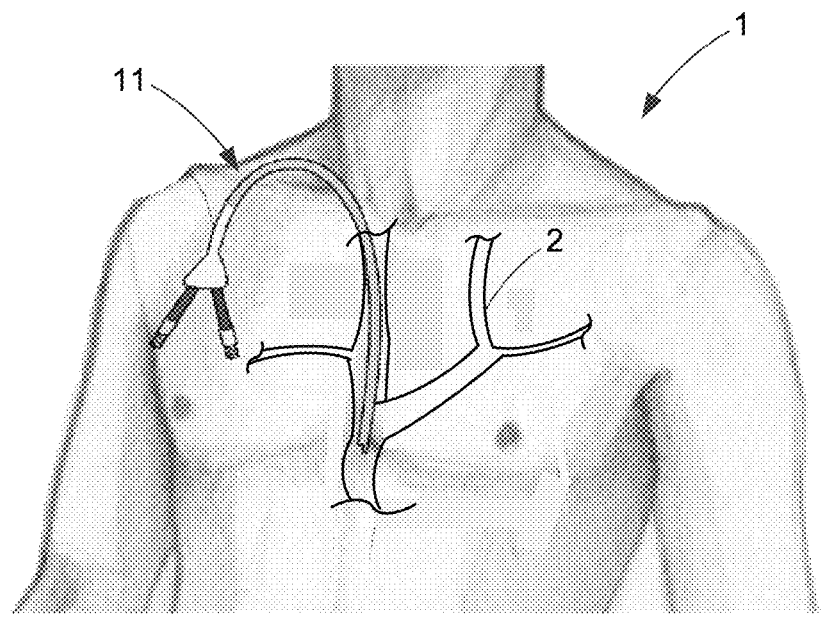
FIG. 2 illustrates a dialysis catheter with the distal tip positioned near the heart in the chest.

FIG. 2 illustrates the standard dialysis catheter 11 implanted in a patient's 1 chest near the heart, with the distal tips of the aspiration tube 18 and the injection tube 19 inserted into the patient's chest 1 superior vena cava blood vessel 2.

Figure 3:
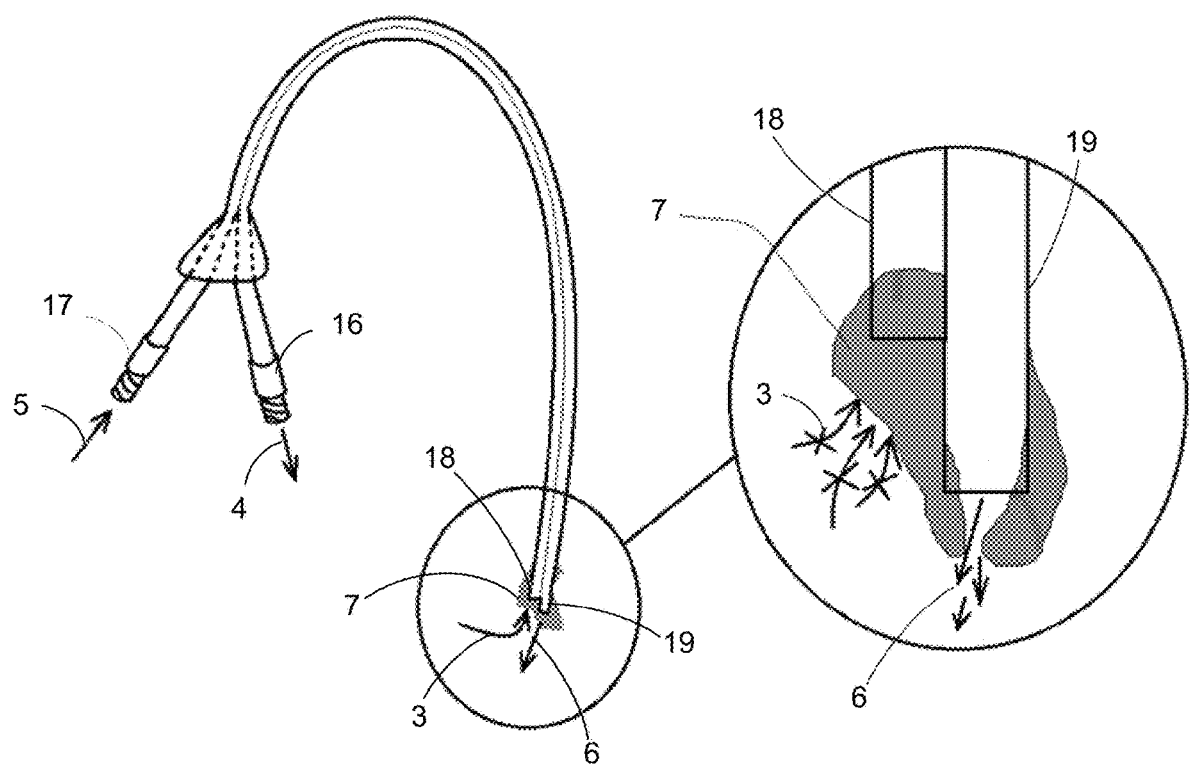
FIG. 3 illustrates an occluded dialysis catheter with development of fibrin and clot at the distal tip.

FIG. 3 illustrates how the fibrin and clot 7 developed on the distal tips of the aspiration tube 18 and the injection tube 19 restricting the flow of the patient's blood through the standard dialysis catheter 11. The patient's blood exiting 6 the distal tip of the injection tube 19 may be able to break the fibrin and clot 7 forming around the distal tip of the injection tube 19 due to pressure. However, the patient's blood entering 3 the distal tip of the aspiration tube 18 cannot pass through the fibrin and clot 7 forming around the distal tip of the aspiration tube 18 due to the ball-valve mechanism.

Figure 4:
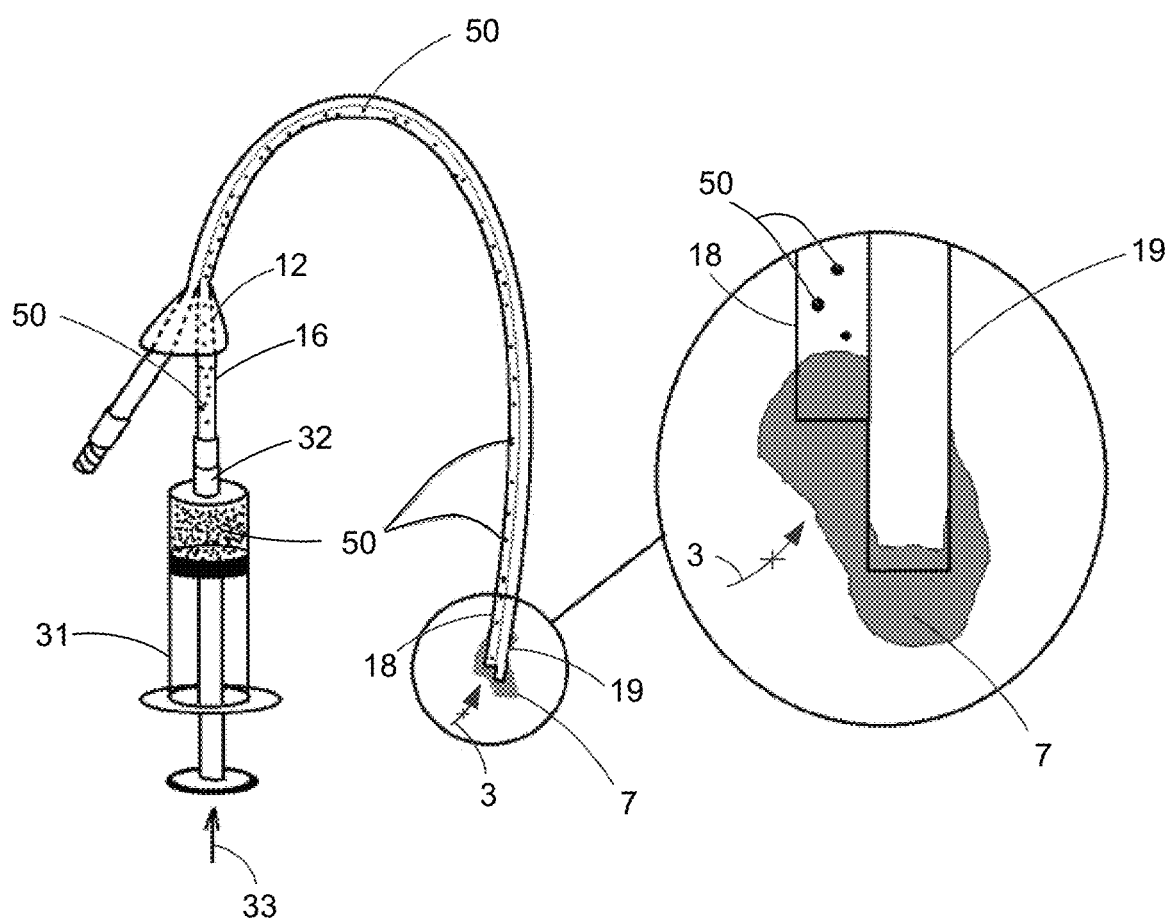
FIG. 4 illustrates an injection of medication into the dialysis catheter port with medication diffusion to the tip.

FIG. 4 illustrates the standard method of restoring patency in the standard dialysis catheter 11. A syringe 31 containing medication 50 attaches to the aspiration port 16 using a standard Luer lock attachment 32. The syringe 31 injects 33 the medication 50 in the aspiration port 16. Pressure from the injection 33 pushes the medication 50 into the aspiration tube 12. This method intends the medication 50 to reach the distal tip of the aspiration tube 18, where the medication 50 breaks down the fibrin and clot 7 to allow the patient's blood to enter 3 the distal tip of the aspiration tube 18. However, this method is ineffective because the injection 33 does not produce enough pressure, resulting in most of the injected medication 50 to remain in the aspiration tube 12 without reaching the distal tip of the aspiration tube 18. The small amount of medication 50 reaching the distal tip of the aspiration tube 18 is not sufficient to break down enough fibrin and clot 7 to allow the patient's blood to enter 3 the distal tip of the aspiration tube 18.

Figure 5:
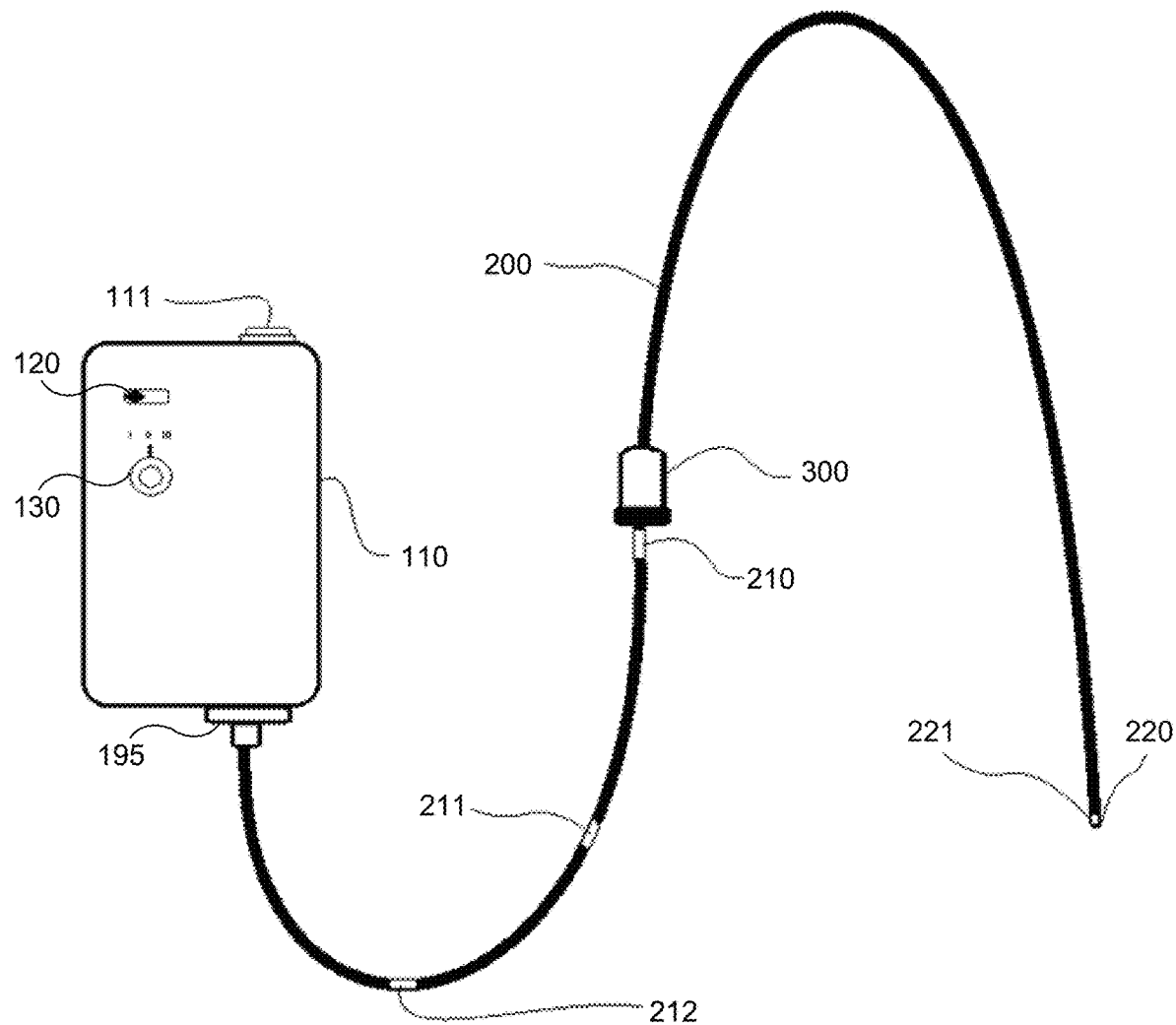
FIG. 5 illustrates the infusion system with the infusion pump and control the preset infusion catheter and the associated components.

FIG. 5 illustrates an embodiment of the catheter clearance device 100, consisting of a catheter clearance box 110 connected to a medication injection port 111 on one end, and an infusion catheter connector 195 on the other end. The infusion catheter connector 195 connects the catheter clearance box 110 to an infusion catheter 200.

The infusion catheter 200 is connected to the catheter clearance box 110 on one end and has a distal tip 220 on the other end. A connector and valve 300 attaches to the infusion catheter 200. The infusion catheter 200 displays placement markers measuring 19 centimeters 210, 23 centimeters 211, and 27 centimeters 212 respectively from the distal tip 220 of the infusion catheter 200. The distal tip 220 of the infusion catheter 200 contains a radiopaque marker 221, which can be detected by x-ray.

A port switch 120 on the catheter clearance box 110 turns the catheter clearance device 100 on and off. A flow rate control selector 130 on the catheter clearance box 110 controls the speed at which medication travels from the catheter clearance box 110 to the distal tip 220 of the infusion catheter 200.

Figure 6:
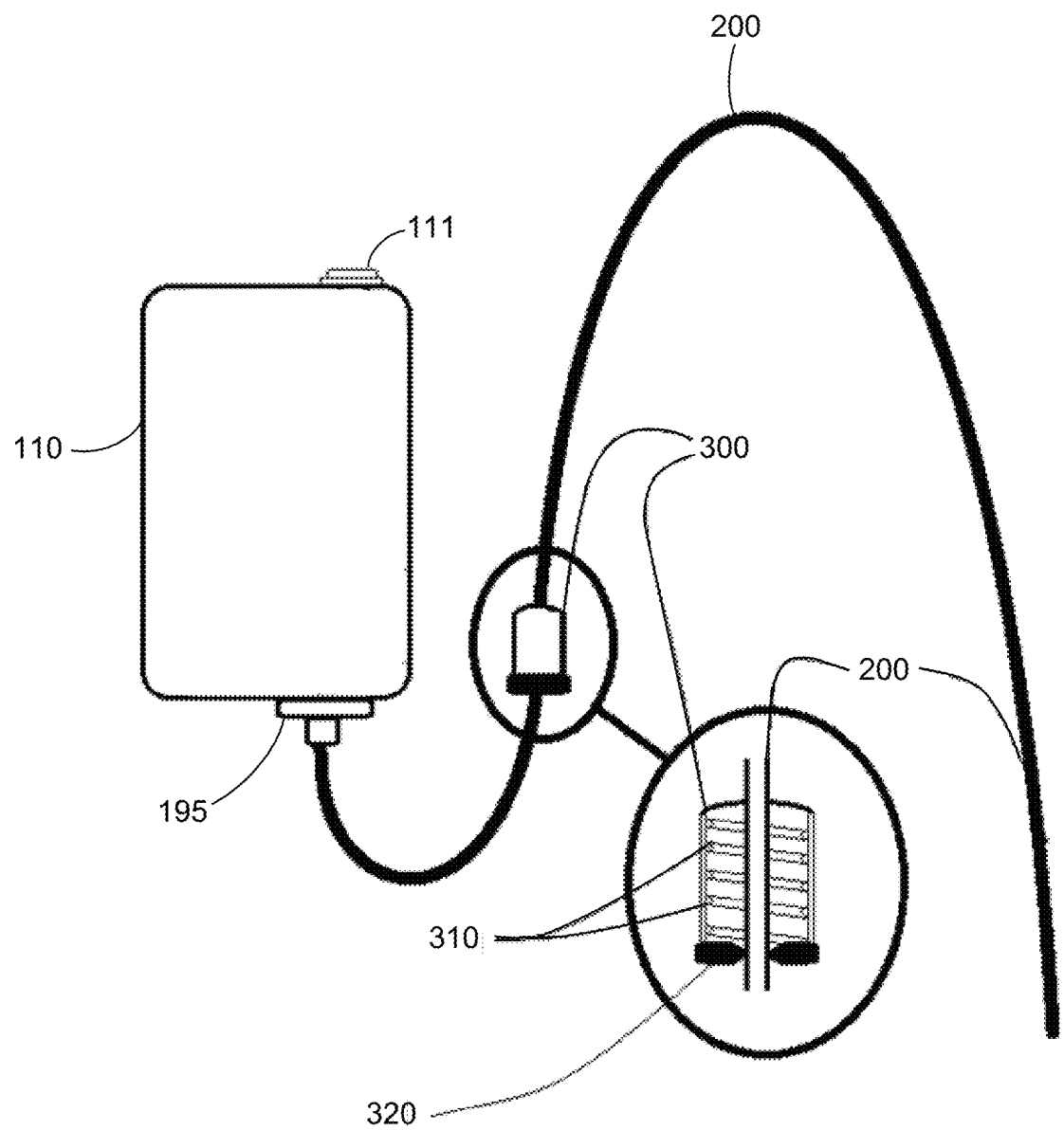
FIG. 6 illustrates an anti-leak connector with internal Luer lock connector and anti-leak valve sealing around the infusion catheter.

FIG. 6 illustrates the connector and valve 300, which is attached to the infusion catheter 200 and can be moved along the length of the infusion catheter 200 for proper placement of the infusion catheter 200 inside standard dialysis catheters. The connector and valve 300 consist of a female Luer lock connector 310 and an anti-leak valve 320. The female Luer lock connector 310 can attach to the aspiration port 16 of a standard dialysis catheter 11. The anti-leak valve 320 can seal the outer portion of the infusion catheter 200. When fully sealed, the anti-leak valve 320 prevents the flow of medication inside the infusion catheter 200 from escaping, thus directing the medication to the clot.

Figure 7:
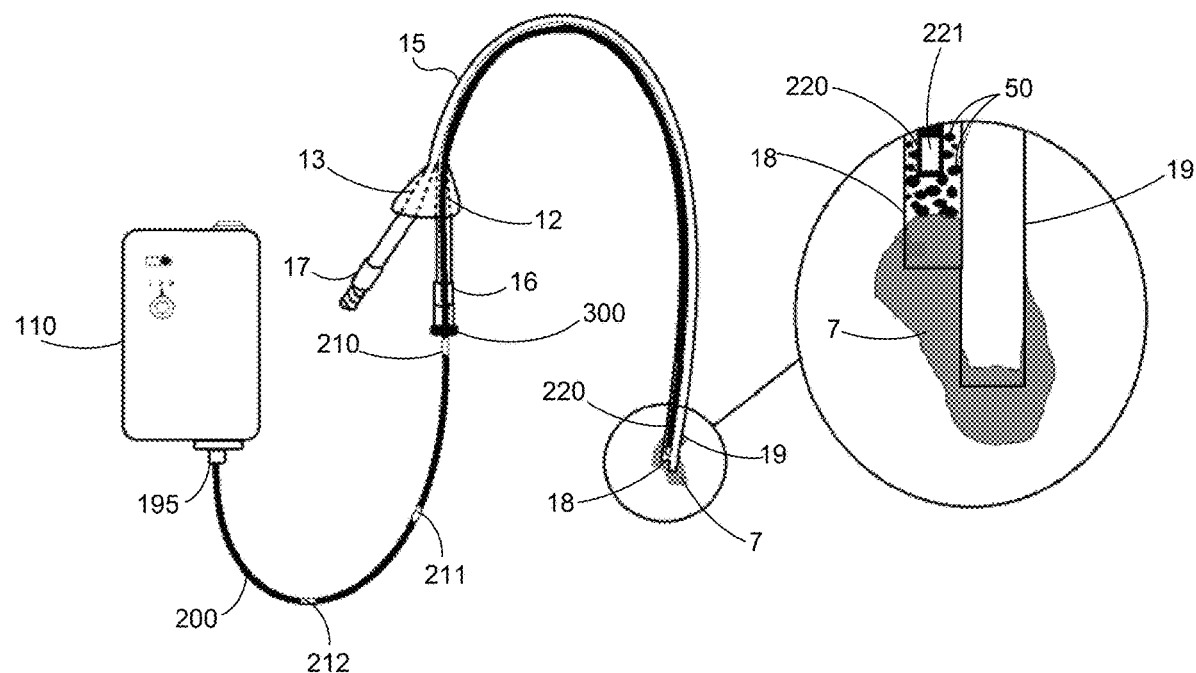
FIG. 7 illustrates an infusion system deployed with the tip in the dialysis catheter and medication infused directly at the dialysis catheter tip.

FIG. 7 illustrates the placement of the catheter clearance device 100 inside the aspiration tube 12 of a standard dialysis catheter 11. Specifically, the infusion catheter 200 is inserted into the catheter 15 of the standard dialysis catheter 11 through the aspiration port 16. The catheter clearance device 100 is correctly placed inside a standard dialysis catheter 11 when the distal tip 220 of the infusion catheter 200 reaches the distal tip of the aspiration tube 18. In this illustration, the first placement marker 210 confirms this correct placement when the placement marker 210 is positioned directly underneath the aspiration port 16 of the standard dialysis catheter 11. The correct placement can also be confirmed by an x-ray showing the radiopaque marker 221 is aligned with the distal tip of the aspiration tube 18 of the standard dialysis catheter 11. The connector and valve 300 attaches to the aspiration port 16 to secure the infusion catheter 200 inside the catheter 15 of the standard dialysis catheter 11 once correct placement is confirmed. The catheter clearance device 100 can also be placed inside the injection tube 13 of the standard dialysis catheter 11 using the same method described above.

Figure 8:
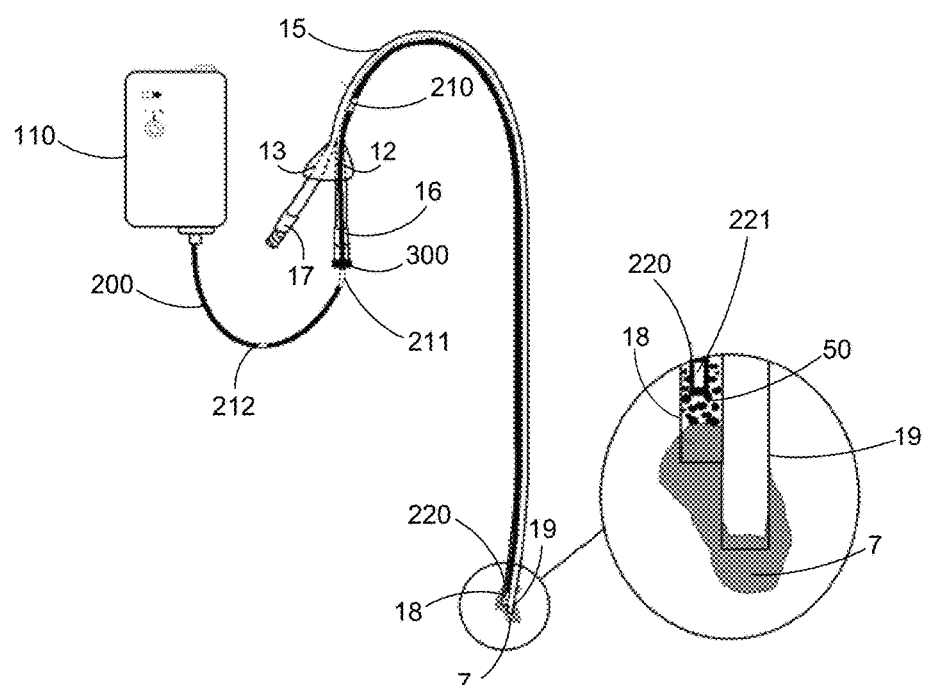
FIG. 8 illustrates the infusion system deployed within a longer dialysis catheter confirmed by the matched infusion catheter marker.

FIG. 8 illustrates the placement of the catheter clearance device 100 inside a standard dialysis catheter 11 with a longer catheter 15, such that the infusion catheter 200 is advanced until the second placement marker 211.

Figure 9:
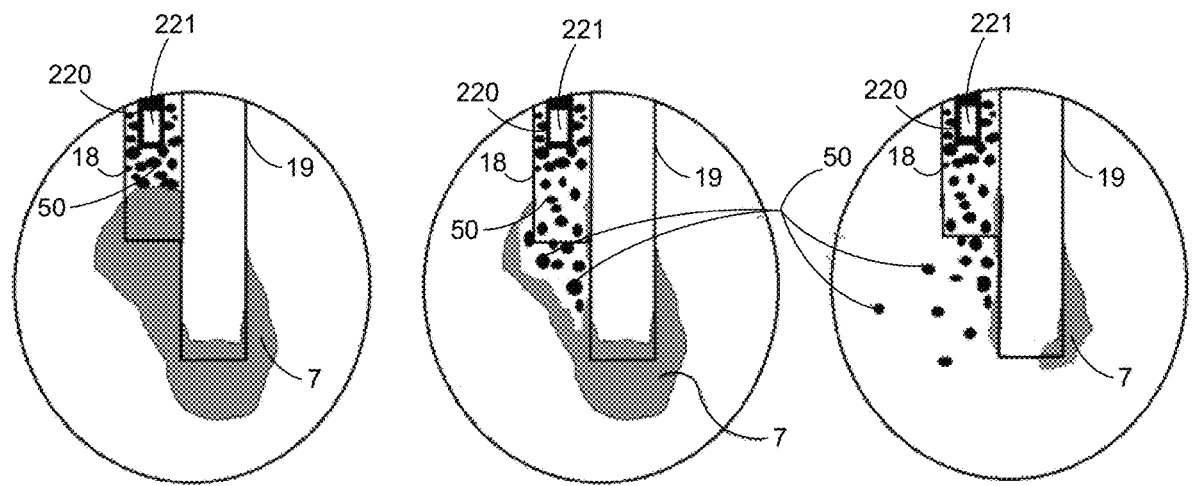
FIG. 9 illustrates the lysis process, from left to right wherein the medication dissolves the fibrin and clot and restored catheter patency.

FIG. 9 the infusion of the medication 50 to the distal tip of the aspiration tube 18 of the standard dialysis catheter 11. The distal tip 220 of the infusion catheter 200 ensures delivery of all injected medication 50 directly to the distal tip of the aspiration tube 18. Thus, there will be sufficient medication 50 to dissolve the fibrin and clot 7, restoring patency to the standard dialysis catheter 11.

Figure 10:
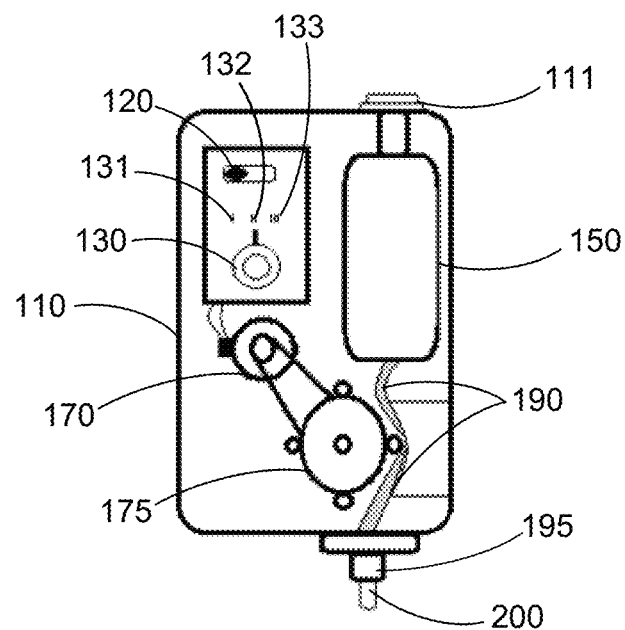
FIG. 10 illustrates an inside view of the infusion pump system with internal components visualized.

FIG. 10 illustrates the interior of the catheter clearance box 110. The medication injection port 111 at the top of the catheter clearance box 110 is connected to a medication reservoir 150. In one embodiment of the invention, the medication reservoir 150 is made of an evacuated compliant sac structure that expands as it accepts fluids. This embodiment eliminates air in the system. The other end of the medication reservoir 150 is connected to an outflow line 190. The other end of the outflow line 190 is connected to the infusion catheter connector 195. The infusion catheter 200 attaches to the other end of the infusion catheter connector 195. The port switch 120 is connected to the motor 170. The motor is connected to the belt and infusion gear 175.

The flow rate control selector 130 displays three flow rate options on the exterior of the catheter clearance box 110. The three respective flow rate options are minimum 131, medium 132, and maximum 133. On the interior of the catheter clearance box 110, the flow rate control selector 130 is connected to the motor 170.

Figure 11:
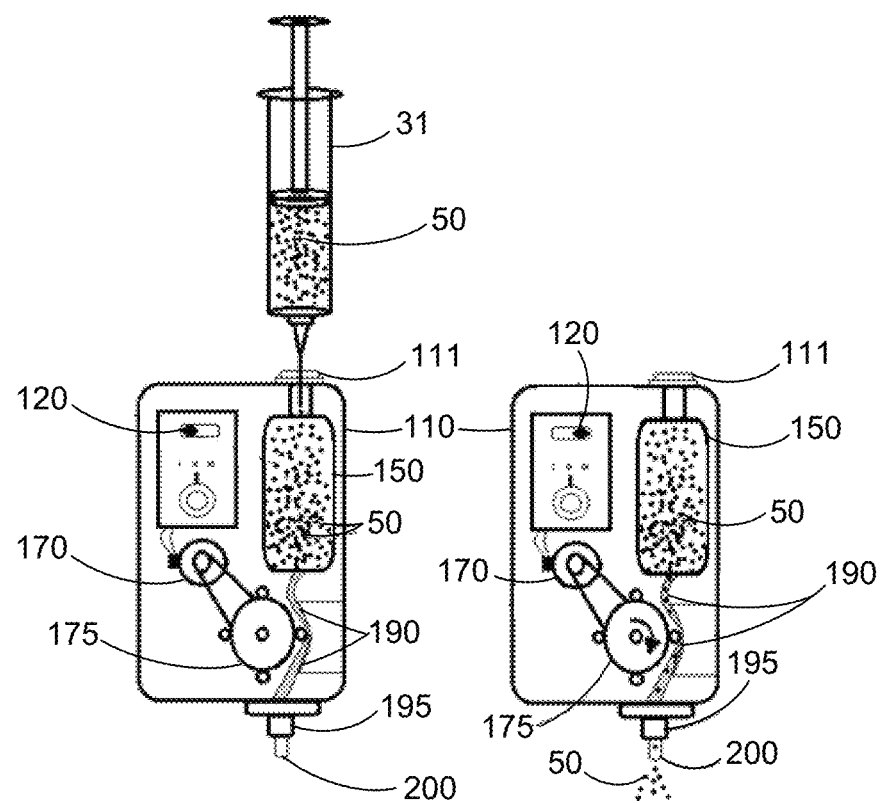
FIG. 11 illustrates the components housed within the Infusion system, a medication reservoir and output catheter and the infusion controls with electronically controlled motor and pump mechanism.

FIG. 11 illustrates how medication 50 travels through the catheter clearance box 110. Specifically, a syringe 31 injects 33 medication 50 through the medication injection port 111. The medication 50 then flows into the medication reservoir 150.

When the port switch 120 is on, the motor 170 powers the belt and infusion gear 175 to rotate. The belt and infusion gear 175 pushes the medication 50 in the medication reservoir 150 through the outflow line 190 to the infusion catheter connector 195, where the medication 50 flows into the infusion catheter 200.

Figure 12:
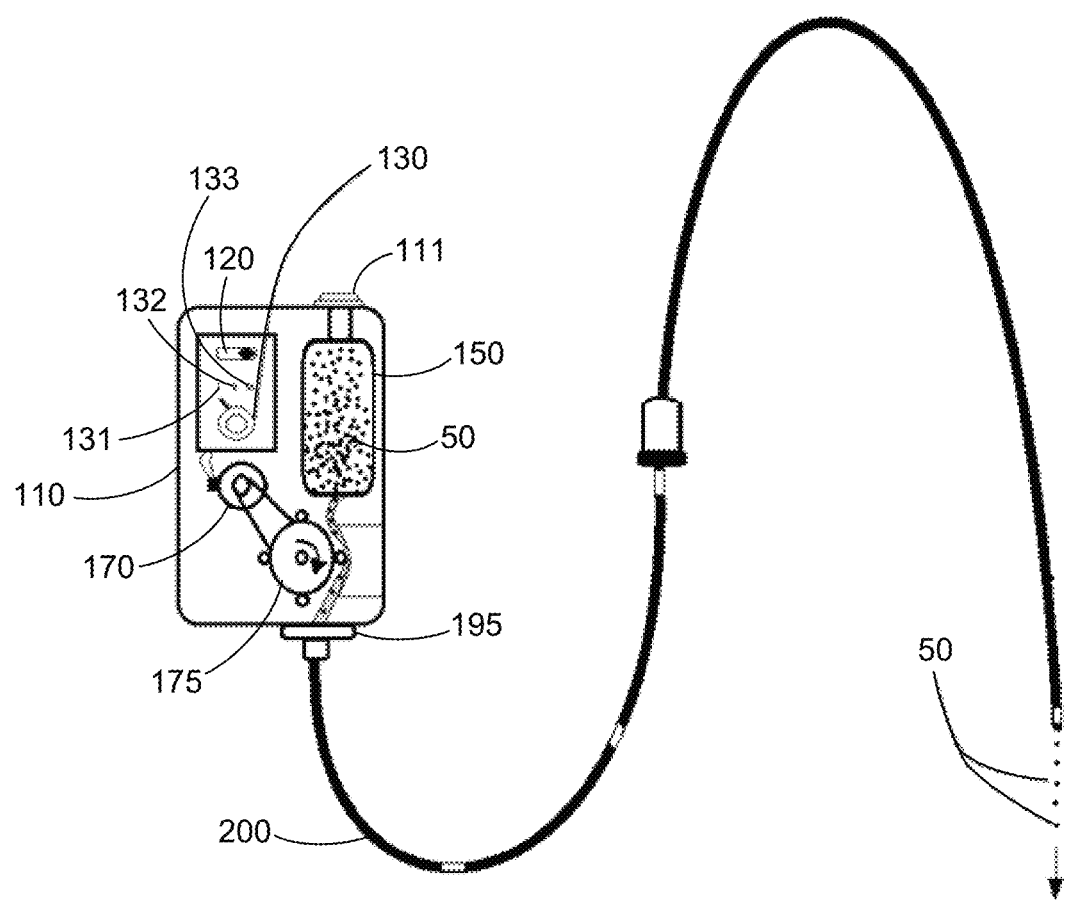
FIG. 12 illustrates a flow rate control sensory set on low with minimal medication output.

FIG. 12 illustrates the catheter clearance device 100 operating on minimum 131. Specifically, when the flow rate control selector 130 is set to minimum 131 and the port switch 120 is on, the motor 170 powers the belt and infusion gear 175 that rotates at a slow speed. As a result, the medication in the medication reservoir 150 is slowly pushed into the outflow line 190, then through the infusion catheter connector 195 into the infusion catheter 200, eventually reaching the distal tip 220 of the infusion catheter 200 and exiting the infusion catheter 200 at a slow rate.

Figure 13:
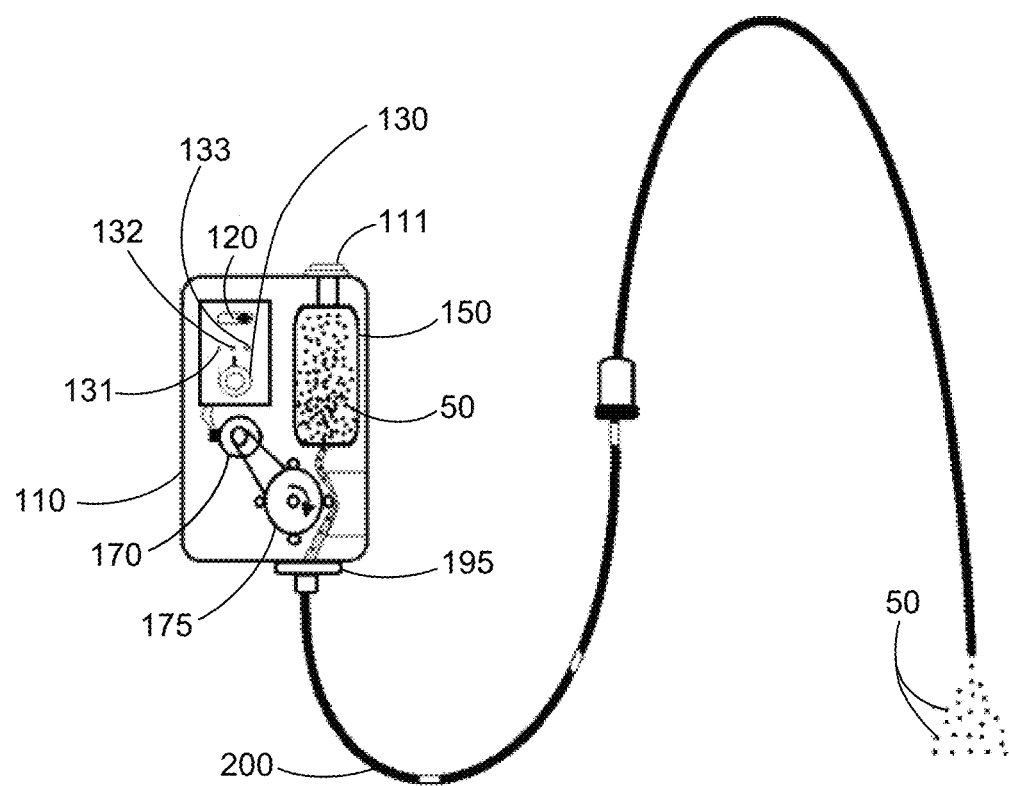
FIG. 13 illustrates a flow rate control sensory set on medium with moderate medication output.

FIG. 13 illustrates the catheter clearance device 100 operating on medium 132. Specifically, when the flow rate control selector 130 is set to medium 132 and the port switch 120 is on, the motor 170 powers the belt and infusion gear 175 that rotates at a medium speed. As a result, the medication in the medication reservoir 150 is pushed into the outflow line 190 at a medium speed, then through the infusion catheter connector 195 into the infusion catheter 200, eventually reaching the distal tip 220 of the infusion catheter 200 and exiting the infusion catheter 200 at a medium rate. The medication may exit the infusion catheter through a nozzle, which may comprise any type opening at the distal end of the infusion catheter through which medication pass out of the infusion catheter 200.

Figure 14:
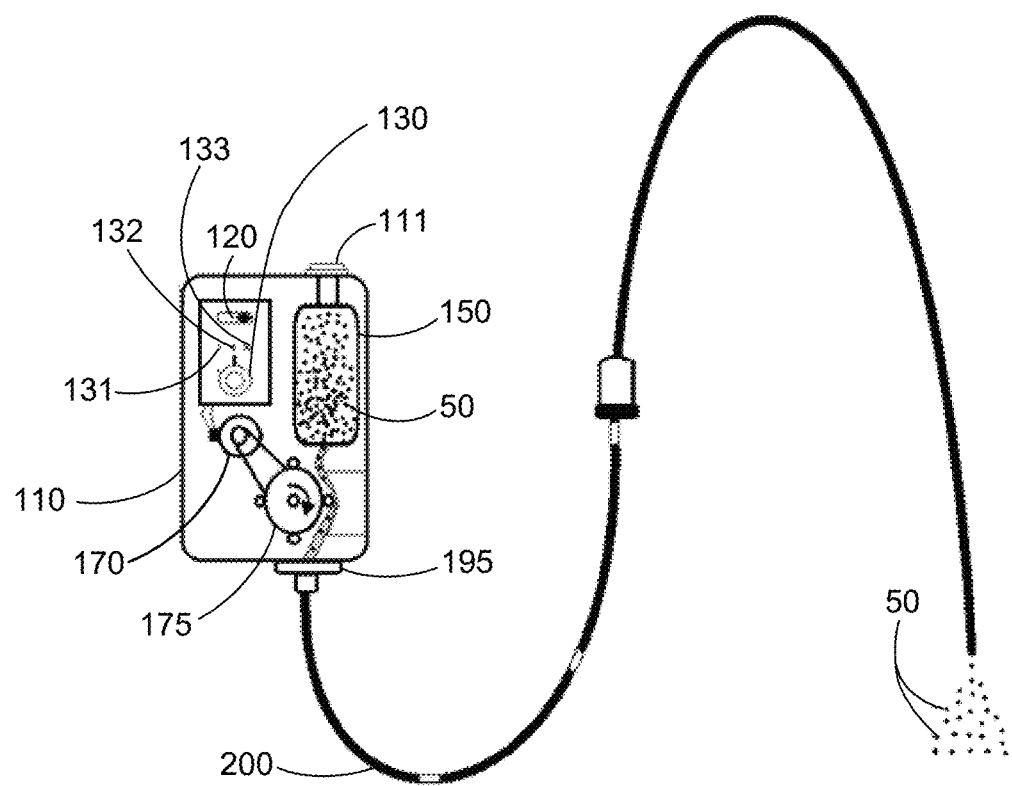
FIG. 14 illustrates a flow rate control sensory set on high with maximum medication output.

FIG. 14 illustrates the catheter clearance device 100 operating on maximum 133. Specifically, when the flow rate control selector 130 is set to maximum 133 and the port switch 120 is on, the motor 170 powers the belt and infusion gear 175 that rotates at a high speed. As a result, the medication in the medication reservoir 150 is pushed into the outflow line 190 at a high speed, then through the infusion catheter connector 195 into the infusion catheter 200, eventually reaching the distal tip of the infusion catheter 200 and exiting the infusion catheter 200 at a fast rate.

Figure 15:
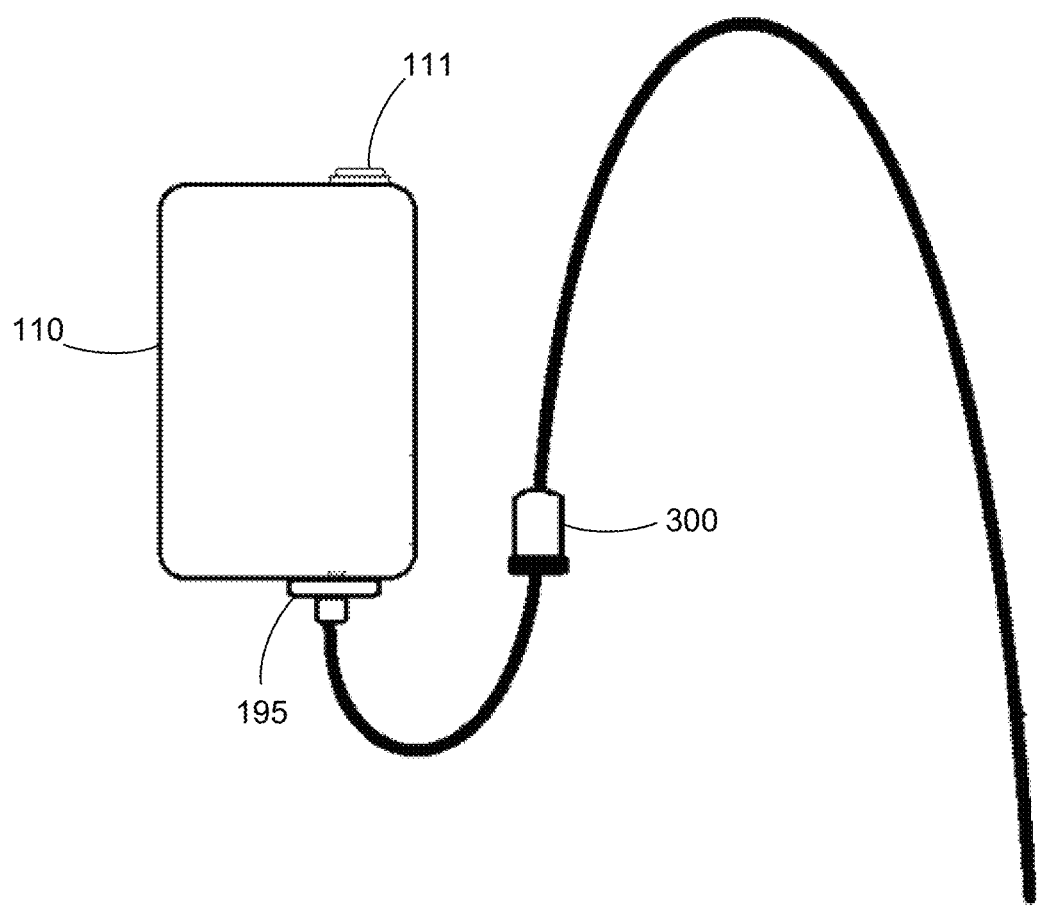
FIG. 15 illustrates an additional embodiment of the infusion system with a predetermined, non-adjustable catheter length and anti-leak connecter.

FIG. 15 illustrates another embodiment of the catheter clearance device 100 using a premeasured infusion catheter 200, which does not display placement markers 210, 211, 212. The placement of the connector and valve 300 is preset such that the connector and valve 300 cannot move along the infusion catheter 200. Such infusion catheters 200 vary in length and are based on the length of catheters on standard dialysis catheters 11. Using this embodiment, the user would choose the appropriate length of a premeasured infusion catheter 200 to insert into the infusion catheter connector 195.

Figure 16:
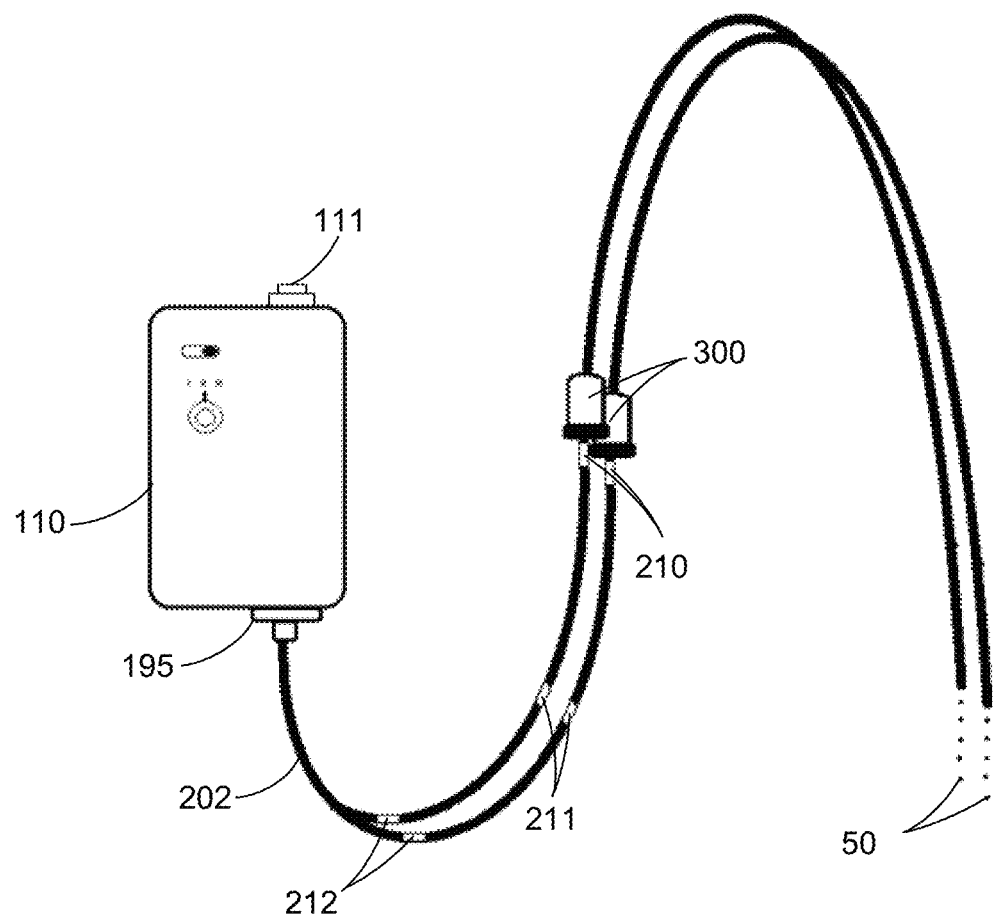
FIG. 16 illustrates an additional embodiment of the infusion system with two outflow catheters.

FIG. 16 illustrates another embodiment of the catheter clearance device 100 where a 2-prong infusion catheter 202 is attached to the infusion catheter connector 195. The 2-prong infusion catheter 202 splits into two tubes, each tube displaying three placement markers 210, 211, 212. A connector and valve 300 are attached to each tube. This embodiment allows the catheter clearance device 100 to be placed inside both the aspiration tube 12 and the injection of a standard dialysis catheter 11, such that a single catheter clearance device 100 can remove fibrin and clot 7 at the distal tips of the aspiration tube 18 and the injection tube 13 of the standard dialysis catheter 11 simultaneously.

Figure 17:
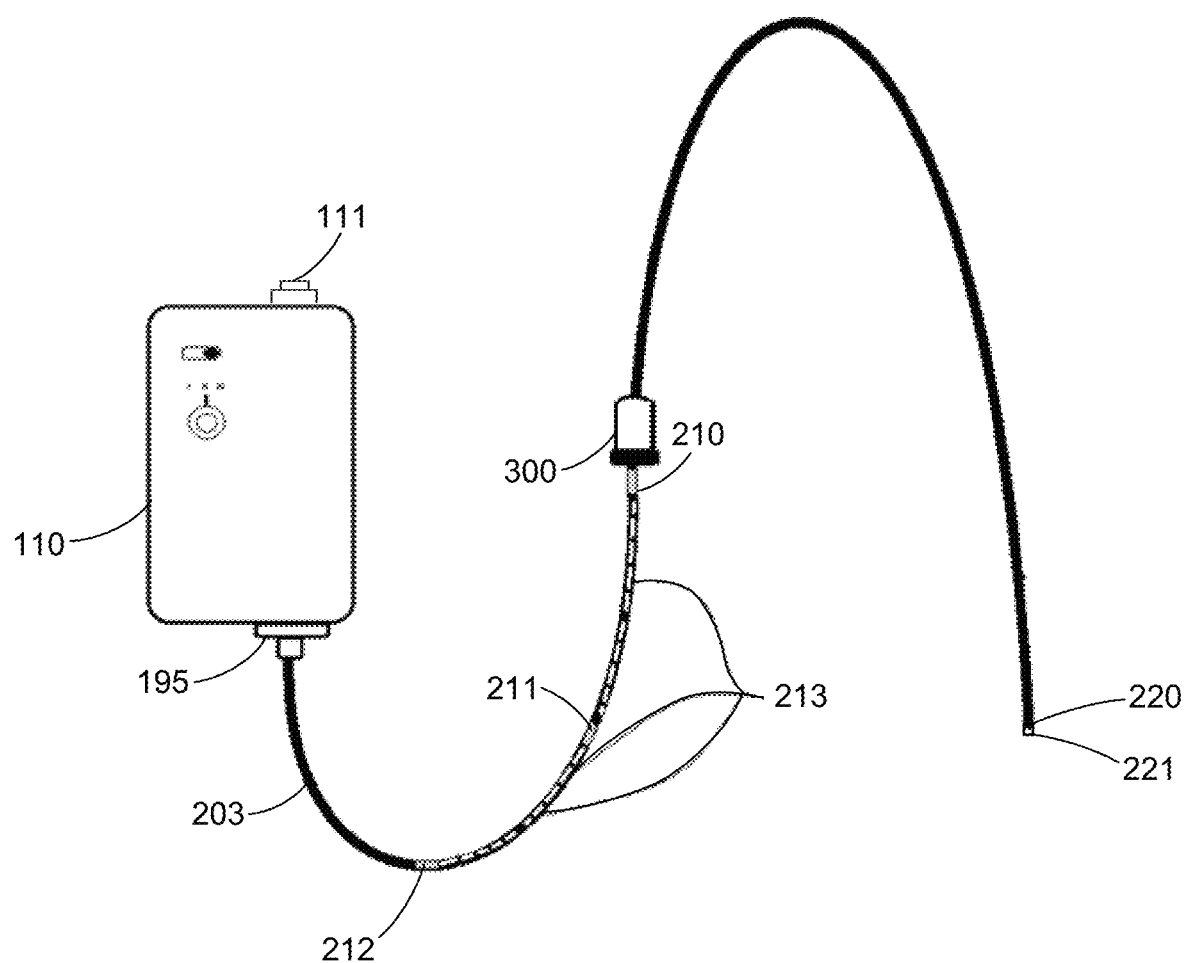
FIG. 17 illustrates an additional embodiment of the infusion system with measurement markers along the proximal infusion catheter.

FIG. 17 illustrates another embodiment of the catheter clearance device 100 where an Infusion catheter with measuring marks 203 is attached to the infusion catheter connector 195. In this embodiment, measuring marks 213 are displayed between the placement markers 210, 211, 212 such that the catheter clearance device 100 can restore the patency of dialysis catheters with non-standard length catheters. The measuring marks 213 may also help adjust the placement of the infusion catheter 200 inside the catheter 15 of a standard dialysis catheter 11, should an x-ray of the radiopaque marker 221 indicate the radiopaque marker 221 is not fully aligned with the distal tip of the aspiration tube 18 or the injection tube 13 of a standard dialysis catheter 11.

Figure 18:
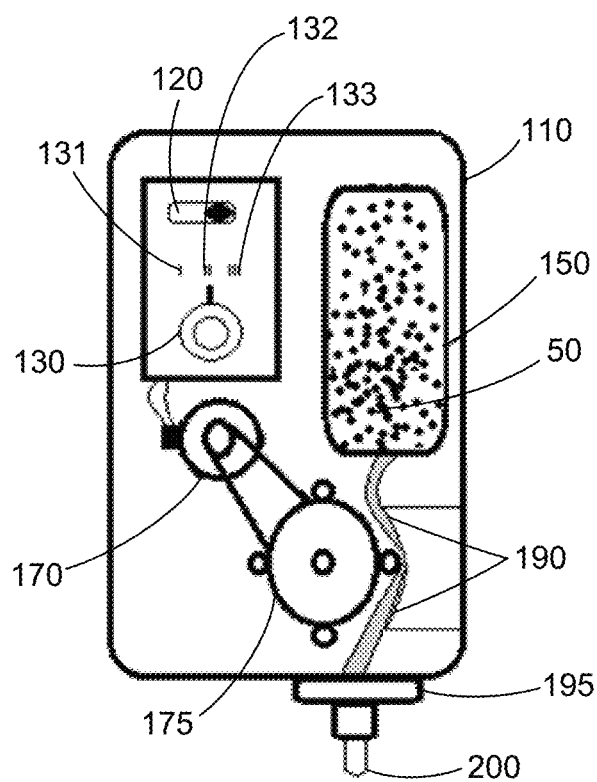
FIG. 18 illustrates an infusion system that is preloaded with a dose of the medication therefore not requiring the infusion port.

FIG. 18 illustrates another embodiment of the catheter clearance device 100 with no medication injection port 111 on the catheter clearance box 110. In this embodiment, the medication reservoir 150 is preloaded with medication 50. This embodiment allows the user to utilize the catheter clearance device 100 without the need to manually inject 33 medication 50 into the catheter clearance box 110.

Figure 19:
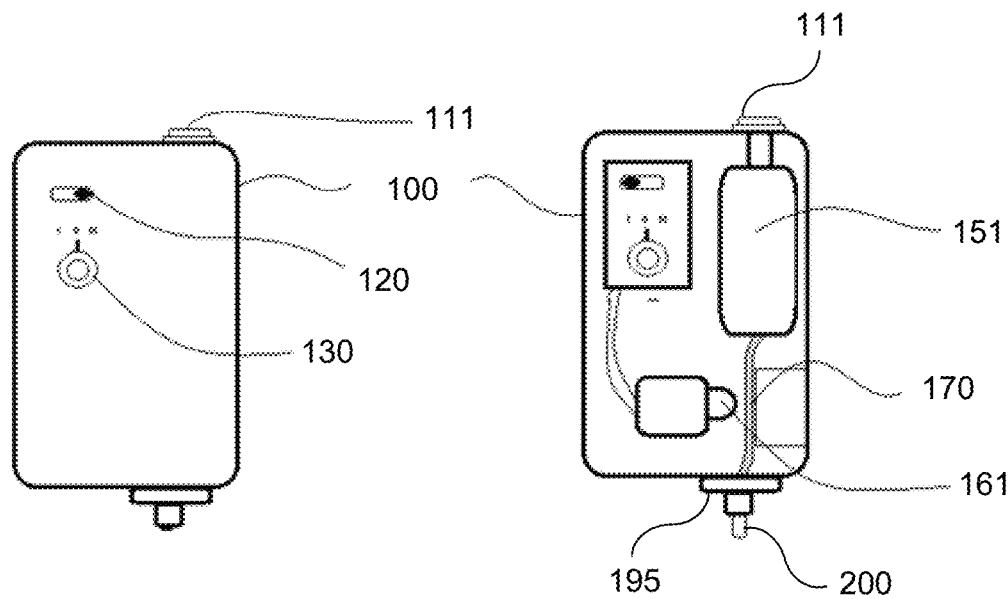
FIG. 19 illustrates an infusion system with minimally compliant drug reservoir and outflow resister unit.

Also disclosed herein are additional embodiments and methods of use. FIG. 19 illustrates the infusion system wherein the minimally compliant drug reservoir 151 is configured to accept an injection through the injection port 111 which expands the reservoir 151 which is then under pressure. Identical reference numbers identify similar elements. The drug then travels from the reservoir 151 through the outflow tubing 170 by passing the outflow resistor plunger 161 and continues into the outflow catheter. In this embodiment, the pump or pusher system may or may not be used. Due to the elastic nature of the reservoir 151, this embodiment will operate without power. The reservoir 151 may have a flow limiting device at its outflow opening which connects the outflow tubing 170. The injection port 111 may be self-sealing to maintain the reservoir 151 free from contamination and maintain pressure in the reservoir.

Figure 20:
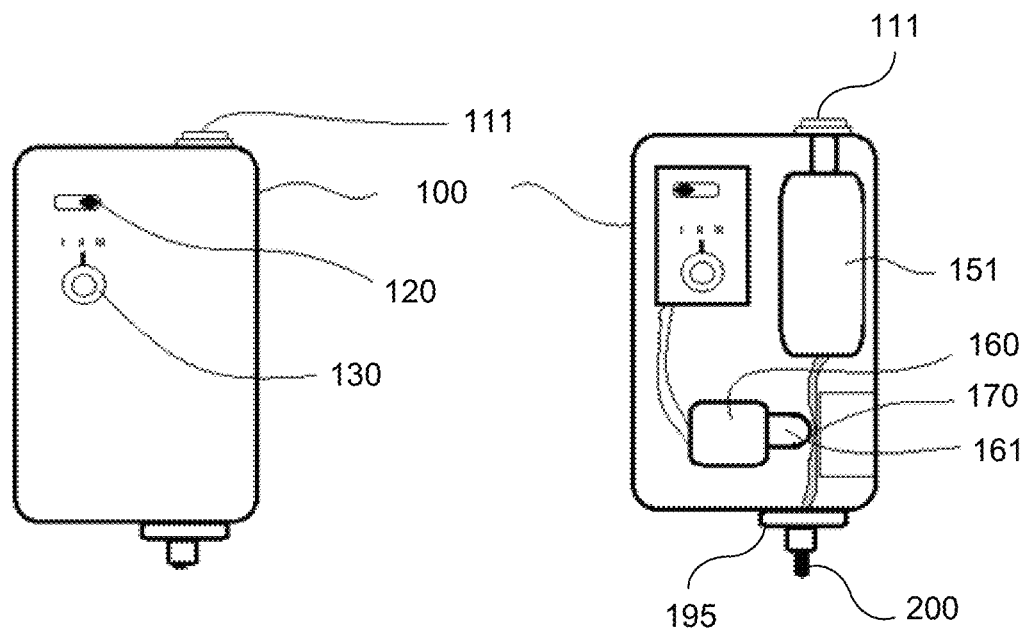
FIG. 20 illustrates and infusion system with minimally compliant drug reservoir and an engaged outflow resister unit compressing outflow tubing.

FIG. 20 illustrates and infusion system with minimally compliant drug reservoir and an engaged outflow resister unit compressing outflow tubing. As shown, the outflow resistor plunger 161 is engaged to contact the outflow tubing 170 thereby providing pressure on the outflow tubing creating resistance slowing and ultimately stopping drug flow through the infusion system. The plunger 161 may be controlled by the flow rate control selector/sensor 130 such that the more the plunger is pushed into the tubing, the less flow is possible and with sufficient plunger movement, flow is entire stopped. The plunger 161 may activate periodically to control flow over time, such as for example, ten minutes every hour, or any other time intervals. The outflow resistor plunger 161 may be controlled by the system of switches 120, 130 and the outflow resistor unit 160. The plunger 161 may be movement controlled by a solenoid, stepper motor, or any other control mechanism. In other embodiments, structures other than a plunger as shown may be used.

Figure 21:
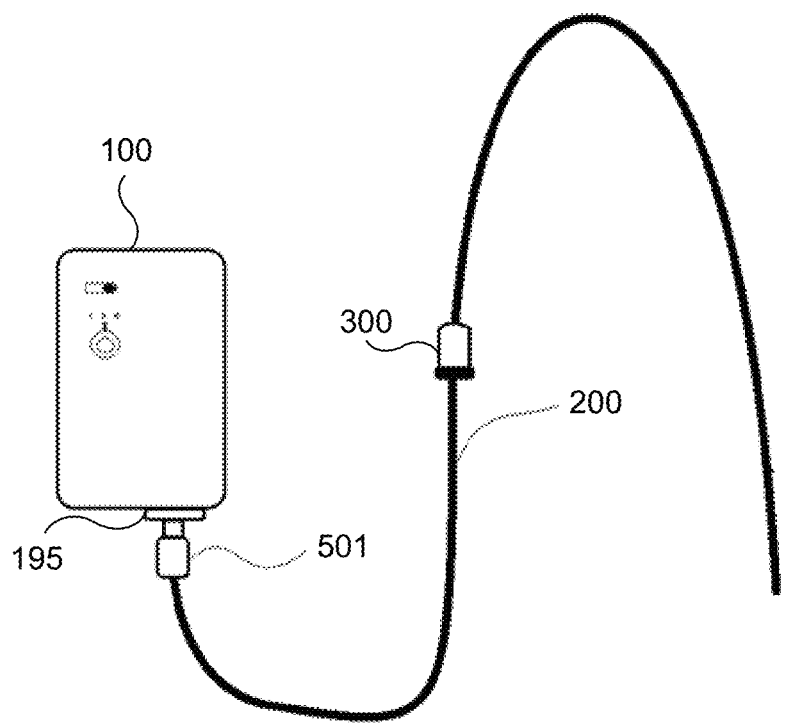
FIG. 21 illustrates a detachable coupling unit separating the catheter from the infusion system.
Figure 22:
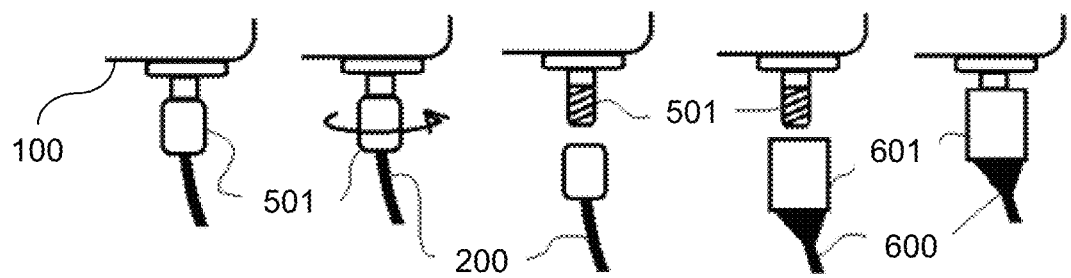
FIG. 22 illustrates a detachable coupling unit and catheter detached from the infusion system Luer lock port as well as a universal catheter coupling attached to the infusion system Luer lock for various types of catheters.

FIG. 21 illustrates a detachable coupling unit separating the catheter from the infusion system. FIG. 22 illustrates a detachable coupling unit and catheter detached from the infusion system Luer lock port as well as a universal catheter coupling attached to the infusion system Luer lock for various types of catheters. FIGS. 21 and 22 illustrate an embodiment having the detachable coupling unit (501) which allows use of any standard catheter with a universal coupling (601) Luer lock type of connector. This allows the user to attach the infusion system directly to an indwelling catheter and perfuse the medication from the proximal end to the distal end without the need for a separate inter-luminal infusion catheter. Although described as a Luer lock type connector, any type or configuration of connector may be used.

Figure 23:
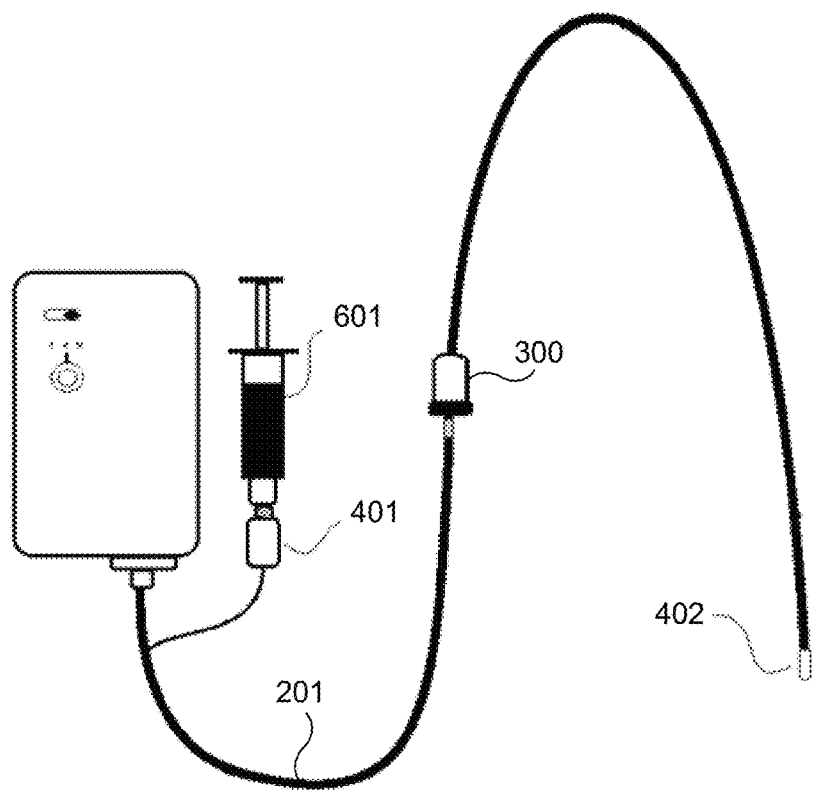
FIG. 23 illustrates a balloon tip in communication with a catheter and a Luer lock engaged by a syringe.

FIG. 23 illustrates a balloon tip in communication with a catheter and a Luer lock engaged by a syringe. As shown, a syringe 400 is filled with a liquid (or air) and in fluid communication with a balloon 402 which is advanced through the infusion catheter 200 to a distal end of the catheter to be just outside of the catheter. The distal tip of the balloon 402 may be advanced into the catheter and further beyond the distal tip by several centimeters. It may be difficult for a user, such as a doctor or nurse, to know the location of the balloon in relation to the end of the infusion catheter 200.

Figure 24:
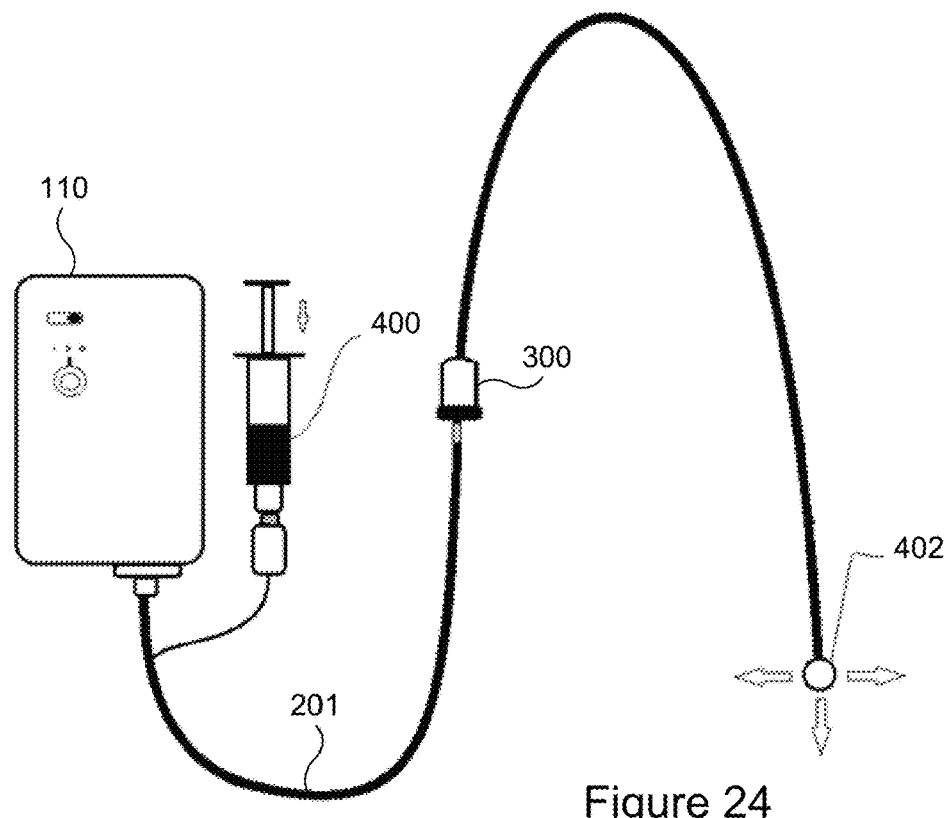
FIG. 24 illustrates an inflated balloon tip when a syringe is depressed to inflate the balloon tip.
Figure 25:
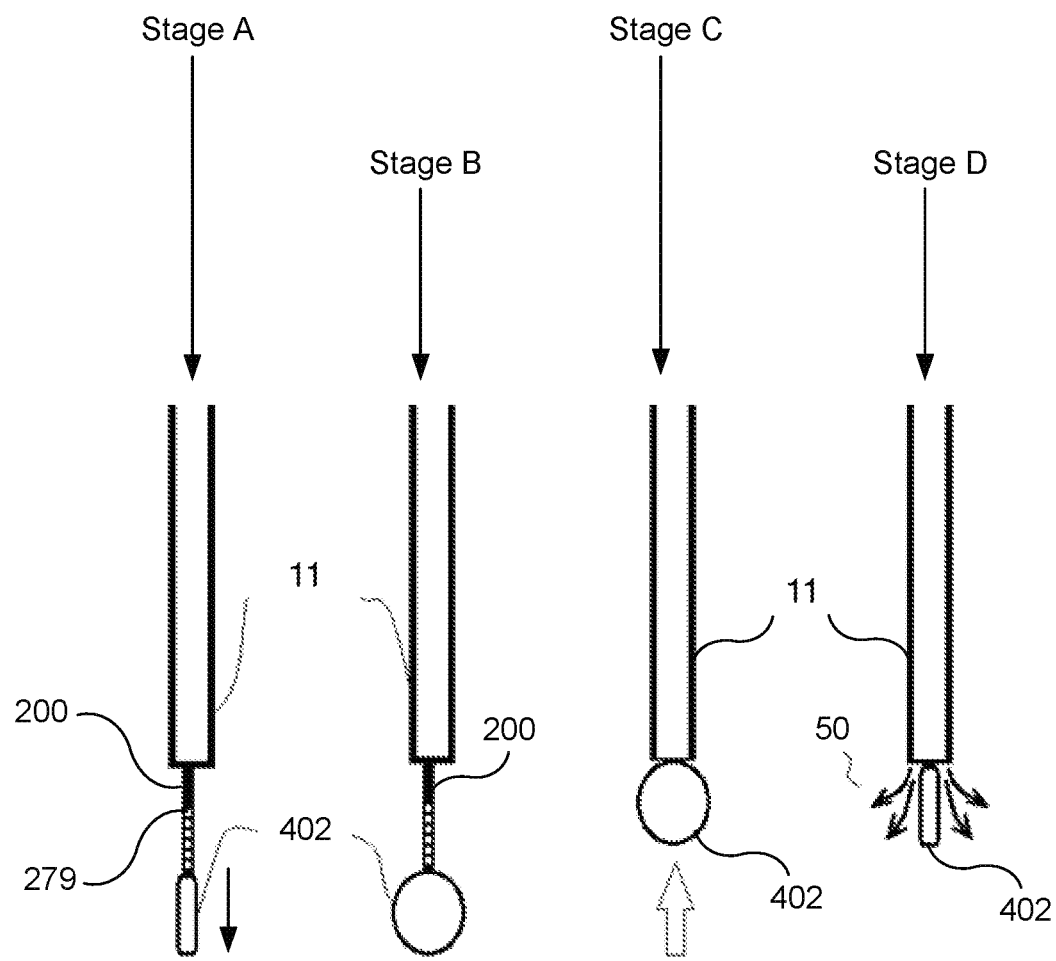
FIG. 25 illustrates a balloon tip deflated and then retracted into a catheter for proper placement prior to drug infusion.

FIG. 24 illustrates an inflated balloon tip when a syringe is depressed to inflate the balloon tip. Depressing the syringe 400 causes the fluid in the syringe to flow into the balloon 402 to thereby inflate the balloon. The balloon 402 may be any shape or size. The balloon 402, once inflated, is pulled back toward the distal end of the catheter 401 until it engages the distal tip 220 of the infusion catheter at which point it is then aligned at the distal dialysis catheter 11 tip to ensure accurate placement. This process is shown in detail in FIG. 25, which illustrates stages A, B, C, and D of the devices at the distal tip. At stage A, a balloon tip is deflated and pushed past the distal end of the dialysis catheter. At stage B, the balloon tip is inflated as shown, and then at stage C, the infusion catheter 200 is retracted back into the dialysis catheter 11. Because the balloon 402 is inflated, it contacts the dialysis catheter 11 to establish proper placement prior to drug infusion. At stage D, the balloon tip is deflated allowing drug infusion 50 to exit the catheter end 11. The drugs exit the infusion catheter 200 through the small openings or ports 279 which are, at stage D, inside the catheter end 11. The flow of the drug clears and dissolves the clot (not shown).

Figure 26:
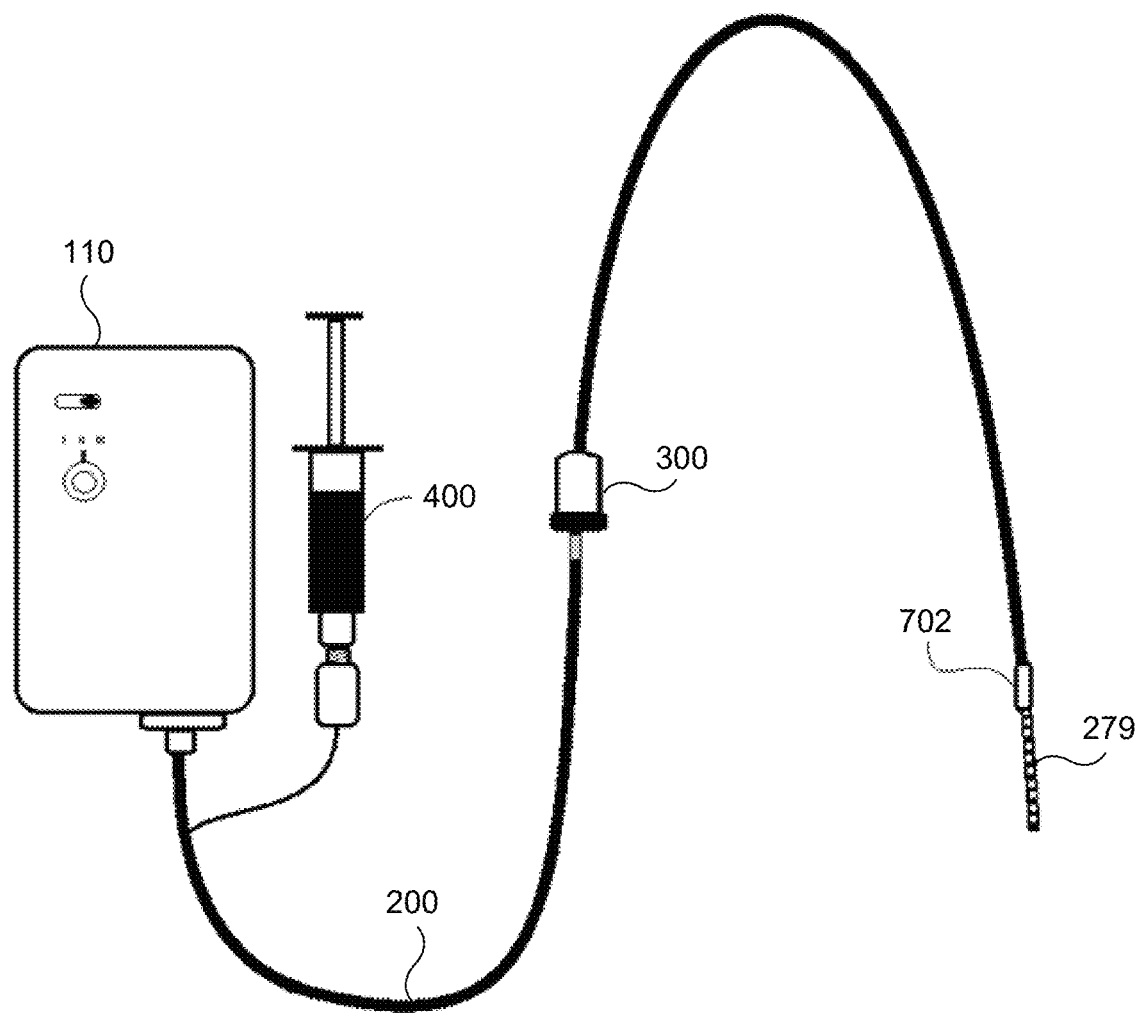
FIG. 26 illustrates a distal balloon with distal infusion capability attached to a syringe.
Figure 27:
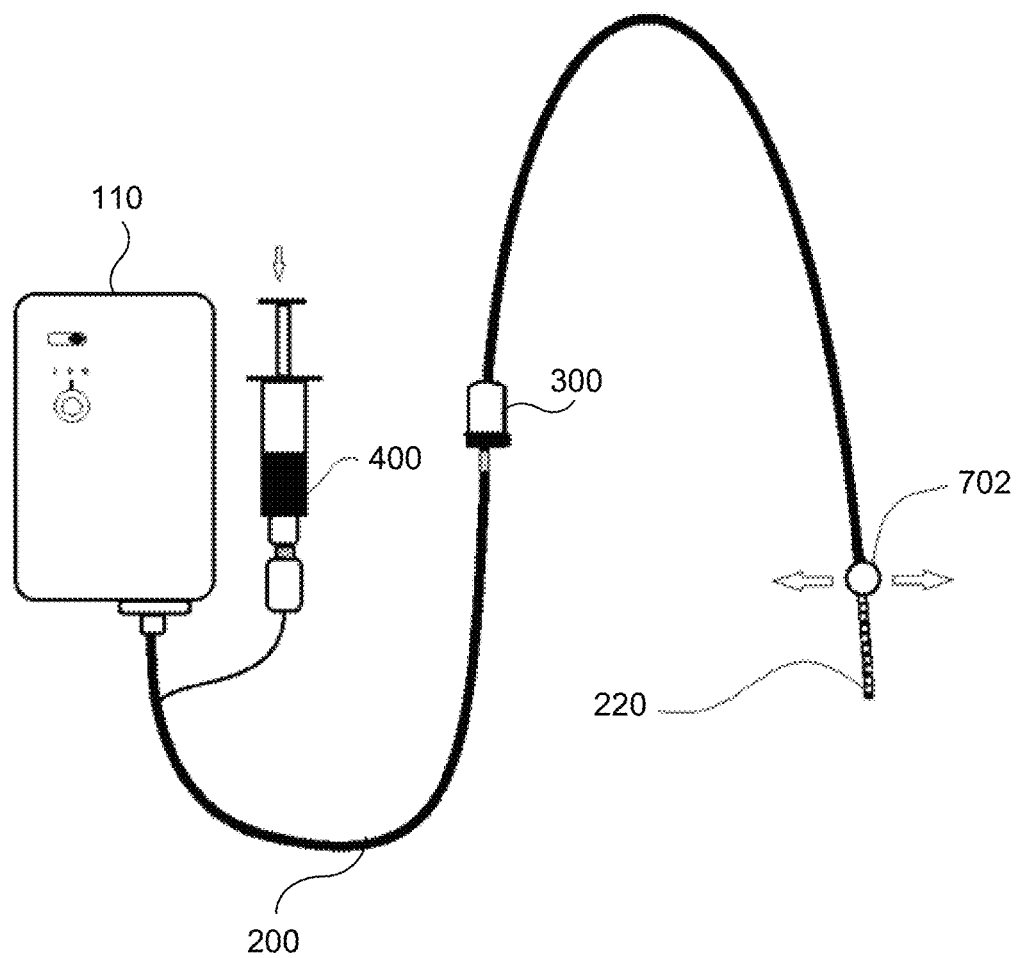
FIG. 27 illustrates an inflated distal balloon, inflated through use of a syringe, extending from a distal end of a catheter.
Figure 28:
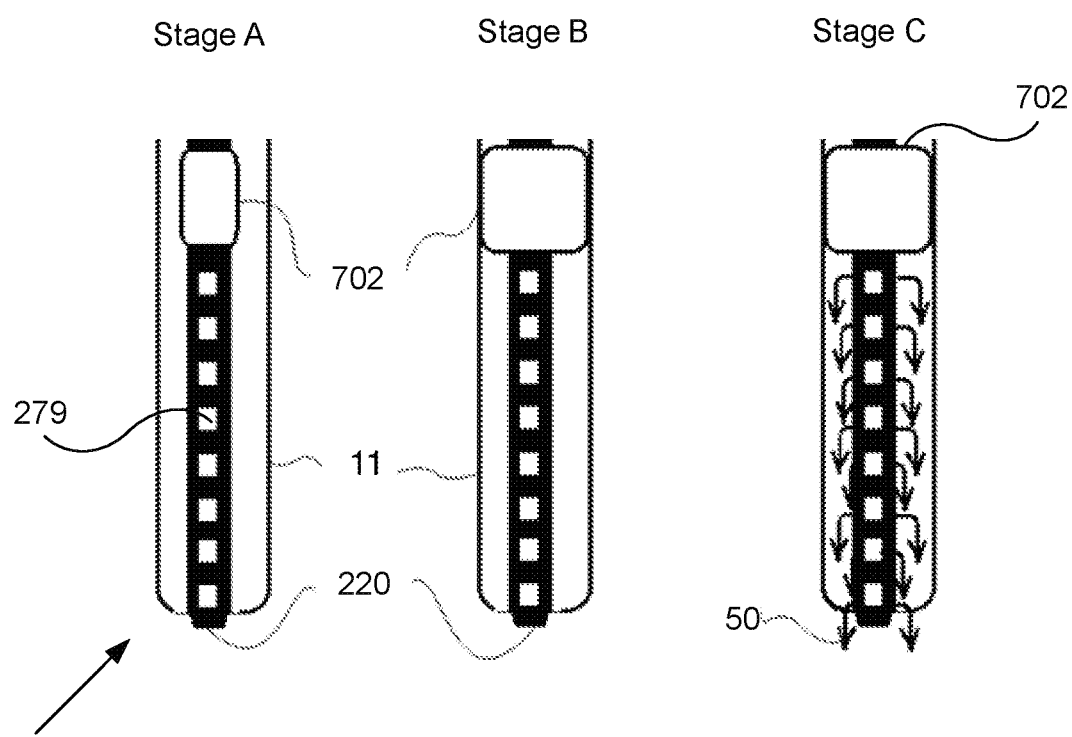
FIG. 28 illustrates an infusion catheter tip, at the distal end of a dialysis catheter, show as deflated, and then inflated, to provide directional drug infusion

FIGS. 26, 27, and 28 discuss an alternative embodiment. FIG. 26 illustrates a distal balloon with distal infusion capability attached to a syringe. In this embodiment, the distal balloon 702 at the distal end of an infusion catheter 200 is inserted through a dialysis catheter (not shown). At the end of the infusion catheter 200 beyond the balloon 702 are numerous openings or ports through which a drug may be ejected or defused to the patient. An infusion system, as discussed above, contains the drug 50 for infusion to the patient. A syringe 400 includes a plunger that contains gas or liquid that is in fluid communication with the balloon 702.

FIG. 27 illustrates an inflated distal balloon, inflated through use of a syringe, extending from a distal end of a catheter. During a subsequent stage, the plunger of the syringe 400 is depressed to inflate the balloon 702. In this embodiment and others, a separate air or fluid pathway may be provided for balloon inflation than is used for the infusion catheter's drug infusion. The balloon, after inflation, may then be pulled back to contact the end of the dialysis withdrawn to the end of the dialysis catheter as occurred in FIG. 25 to properly place the balloon at the end of the dialysis graft.

FIG. 28 illustrates an infusion catheter tip, at the distal end of a dialysis catheter, with the balloon deflated, prior to the balloon being drawn back into the dialysis catheter. In FIG. 28, at a stage A, after accurate placement as shown in FIG. 27, the balloon 702 is deflated and then drawn back into the dialysis catheter 11. The amount the balloon 702, and associated infusion catheter is drawn back into the dialysis catheter may vary subject to the intended function by the physician or nurse. In one embodiment, the balloon is withdrawing 2 centimeters into the distal end of the dialysis catheter 11. In another embodiment, the balloon 702 may be withdrawing an amount equal to the infusion hole section of the infusion catheter. As a stage B, the balloon 702 is inflated to provide a full or partial seal (barrier) between the balloon and the wall of the dialysis catheter 11 to prevent the drug 50, when infused, from escaping back up into the dialysis graft. In this embodiment and others, the syringe 400 or any other device of mechanism may be used to inflate the balloon 702. Then, at stage C, the drug 50 is infused out of the openings 279, such as by depressing the plunger. Because of the inflated balloon 702 the drug 50 is forced out of the end of the dialysis catheter in a single direction outflow and cannot easily travel up into the dialysis catheter.

Figure 29:
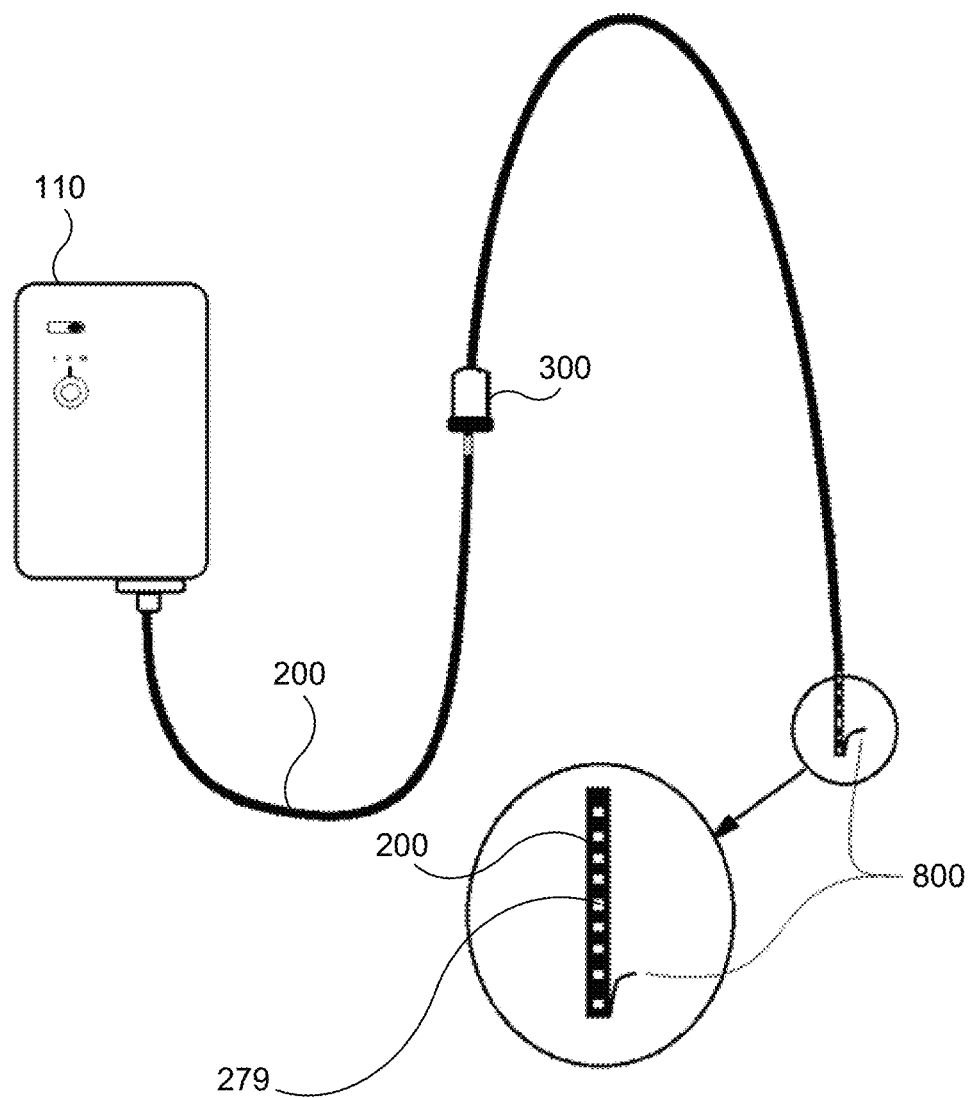
FIG. 29 illustrates a barbed tip at the distal end of an infusion catheter which allows tactile resistance in catheter positioning.
Figures 30A, 30B, 30C, 30D:
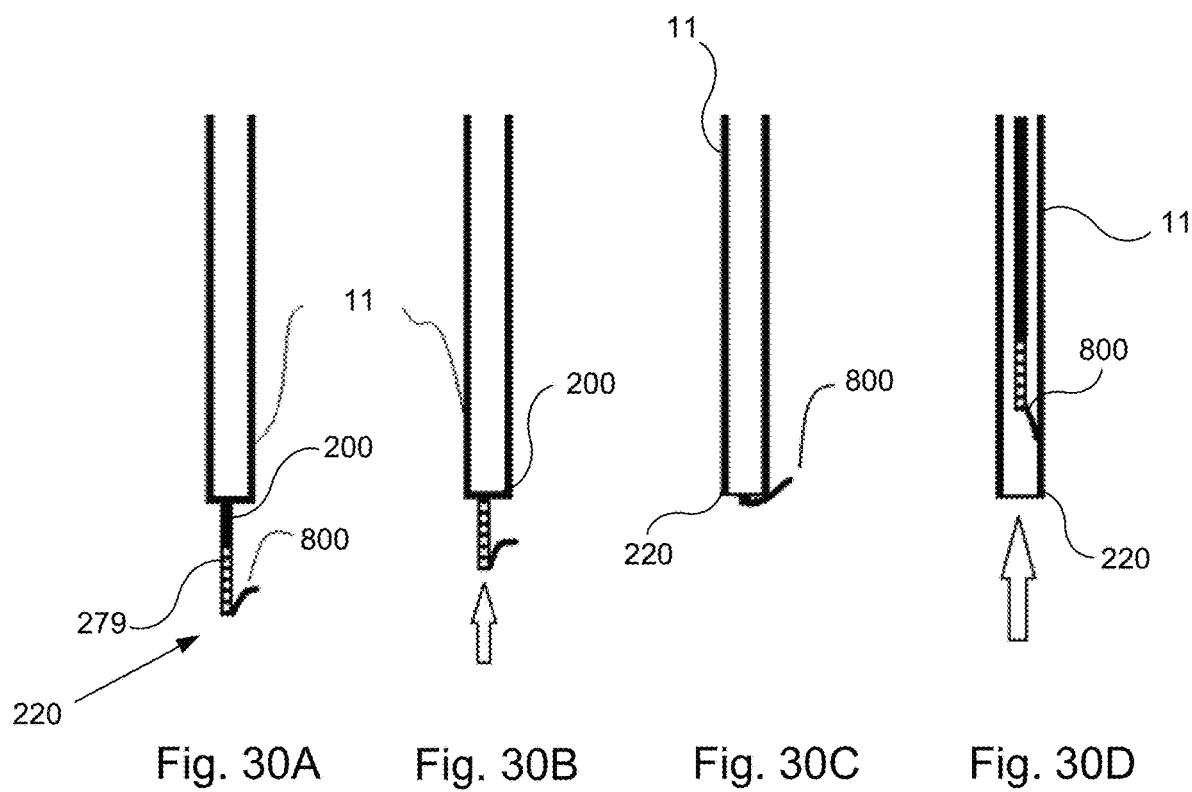
FIG. 30A, FIG. 30B, FIG. 30C, and FIG. 30D illustrate the barbed tip of the infusion catheter positioned at various locations distal to the dialysis catheter

An additional embodiment is illustrated in FIGS. 29 and 30. FIG. 29 illustrates a barbed tip at the distal end of an infusion catheter which allows tactile resistance in catheter positioning. FIGS. 30A, 30B, 30C and 30D illustrates the barbed tip of the infusion catheter positioned at various locations distal to the dialysis catheter.

Drawing 30A shows the barbed tip 800 of the infusion catheter 200 positioned distal to the dialysis catheter 11. FIGS. 30B and 30C illustrates the infusion catheter 200 being pulled back with FIG. 30C showing the barb tip 800 engaging the distal end of the dialysis catheter 11 for correct positioning. FIG. 30D illustrates the retroflexed barb 800 position as the infusion catheter 200 is withdrawn.

In this embodiment, a barb 800 is on the distal tip of the infusion catheter 200. The barb 800 is flexible and flattens parallel to the wall of the distal catheter tip when advanced into the dialysis catheter 11 and then re-expands once it is passed beyond the distal tip as shown in FIG. 30A. The barb 800 may be made from any flexible material with memory, spring characteristics, or elastic properties to return to its expanded position when outside the dialysis catheter 11. One exemplary material is nitinol. Although referred to as a barb 800, the barb may be any type prong or extension from the infusion catheter 200 configured to or capable of functioning as a placement indicator for the infusion catheter.

As shown in FIG. 30B, the infusion catheter 200 is then pulled back from its proximal end until the barb 800 engages the distal end 220 dialysis catheter 11 as shown in FIG. 30C. The user (doctor or nurse) will feel this as increased tension on the infusion catheter 200 and this will then be the optimal position to begin the infusion with the side openings 279 at the tip of the dialysis catheter 11. Alternatively, from the known position of the infusion catheter 200 in relation to the dialysis catheter 11, the user can then move the infusion catheter in to or out of the dialysis catheter 11 of known amount to properly place the distal end of the infusion catheter for optimal drug delivery. Once the infusion is completed, as shown in FIG. 30D, the user pulls the infusion catheter 200 until the barb 800 retroflexes, allowing the infusion catheter to be removed. This embodiment allows the user to position the infusion catheter 200 correctly with the infusion side openings 279 (for drug infusion) at the desired medication deployment site by feeling resistance when pulling back and being able to detect the location of the infusion catheter in relation to the dialysis catheter 11. The infusion catheter is removed by overcoming additional resistance level.

Other systems, methods, features, and advantages of the invention will be or will become apparent to one with skill in the art upon examination of the following figures and detailed description. It is intended that all such additional systems, methods, features, and advantages be included within this description, be within the scope of the invention, and be protected by the accompanying claims.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A dialysis catheter clearance device, for use with a dialysis catheter, comprising:

a medication delivery device configured to selectively output an infusion drug;

an infusion catheter configured to be inserted into a blood vessel of a patient, the infusion catheter having a first end and a second end, the first end of the infusion catheter connected to the medication delivery device, and the second end of the infusion catheter having an opening through which the infusion drug exits the infusion catheter, the infusion catheter also having one or more placement markers for aligning the second end of the infusion catheter with a distal end of the dialysis catheter;

a balloon at a distal tip of the infusion catheter and extending from the distal tip of the infusion catheter away from the infusion catheter, the distal tip being disposed at the second end of the infusion catheter and configured such that the opening of the infusion catheter is disposed between the balloon and the first end of the infusion catheter, the balloon being configured to:

be pushed past the distal end of the dialysis catheter;

expand to an outer width that is greater than an inner width of the dialysis catheter;

retract back toward the distal end of the dialysis catheter and contact the dialysis catheter after expanding to the outer width in order to establish a preferred placement of the infusion catheter, the preferred placement corresponding to the opening of the infusion catheter being inside the distal end of the dialysis catheter in order that a flow of the infusion drug is allowed to exit the distal end of the dialysis catheter for clearing and dissolving a clot, and a flow of blood of the patient is not restricted through the dialysis catheter; and contract to an outer width that is less than an inner width of the dialysis catheter after retracting back toward the distal end of the dialysis catheter;

a balloon inflation device configured to selectively inflate and deflate the balloon; and a tube connecting the balloon and the balloon inflation device to conduct air or fluid to the balloon from the balloon inflation device.

2. The device of claim 1 wherein the balloon inflation device is a syringe, and the tube is connected to the infusion catheter.

3. The device of claim 1 wherein the medication delivery device comprises a catheter clearance box configured to deliver the infusion drug to the infusion catheter, the catheter clearance box having a flow rate control selector, a medication reservoir, and an infusion catheter connector.

4. The device of claim 1 wherein the length of the infusion catheter is premeasured.

5. The device of claim 1 wherein the balloon is configured as a placement guide to provide feedback to a user of a location of the second end of the infusion catheter in relation to the end of the dialysis catheter.

6. The device of claim 1 wherein the infusion catheter includes a Luer lock connector to connect the infusion catheter to the medication delivery device.

7. The device of claim 1 wherein the medication delivery device comprises a syringe.

8. The device of claim 1 wherein the opening of the infusion catheter comprises a plurality of openings configured to disburse clot dissolving medication the infusion drug.

9. The dialysis catheter clearance device of claim 1, further comprising a universal catheter coupling unit between the medication delivery device and the infusion catheter to enable use of different types of catheters with the medication delivery device.

10. The dialysis catheter clearance device according to claim 1, further comprising a valve attached to the infusion catheter, wherein one of the one or more placement markers is configured to be disposed at a proximal end of the valve in order to confirm the preferred placement.

11. The dialysis catheter clearance device according to claim 10, wherein the valve has a Luer lock connector and an anti-leak valve, wherein the Luer lock connector is configured to attach to an aspiration port of the dialysis catheter, and wherein the anti-leak valve is configured to seal an outer portion of the infusion catheter and prevent a flow of the infusion drug from escaping, thus directing the infusion drug to the clot.

12. A dialysis catheter clearance device, for use with a dialysis catheter, comprising:

a medication delivery device configured to selectively output an infusion drug;

an infusion catheter configured to be inserted into a blood vessel of a patient, the infusion catheter having a proximal end and an opposing distal end, the proximal end of the infusion catheter connected to the medication delivery device, and the distal end of the infusion catheter having an opening through which the infusion drug exits the infusion catheter;

an infusion catheter placement device, at a distal tip of the infusion catheter and extending from the distal tip of the infusion catheter away from the infusion catheter, the distal tip being disposed at the second end of the infusion catheter and configured such that the opening of the infusion catheter is disposed between the infusion catheter placement device and the first end of the infusion catheter, the infusion catheter placement device configured to:

be pushed past a distal end of the dialysis catheter;

expand to having an outer width that is greater than an inner width of the dialysis catheter when the infusion catheter placement device is outside the dialysis catheter;

retract back toward the distal end of the dialysis catheter and contact the dialysis catheter after expanding to the outer width in order to establish a preferred placement of the infusion catheter, the preferred placement corresponding to the opening of the infusion catheter being inside the distal end of the dialysis catheter in order that a flow of the infusion drug is allowed to exit the distal end of the dialysis catheter for clearing and dissolving a clot, and a flow of blood of the patient is not restricted through the dialysis catheter; and contract to an outer width that is less than the inner width of the dialysis catheter after retracting back toward the distal end of the dialysis catheter, and when the infusion catheter placement device is inside the dialysis catheter.

13. The device of claim 12 wherein the infusion catheter placement device is a balloon in fluid communication, through a tube, with a balloon inflation and deflation device.

14. The device of claim 12 wherein the medication delivery device comprises a catheter clearance box configured to deliver the infusion drug to the infusion catheter.

15. The device of claim 12 wherein the opening comprises a plurality of openings through which the infusion drug exits the infusion catheter.

16. The device of claim 12 wherein the proximal end of the infusion catheter includes a Luer lock connector to connect the infusion catheter to the medication delivery device.

17. The dialysis catheter clearance device of claim 12, further comprising a universal catheter coupling unit between the medication delivery device and the infusion catheter to enable use of different types of catheters with the medication delivery device.

18. A dialysis catheter clearance device, for use with a dialysis catheter, comprising:
- a medication delivery device configured to selectively output an infusion drug;
- an infusion catheter configured to be inserted into a blood vessel of a patient, the infusion catheter having a first end and a second end, the first end of the infusion catheter connected to the medication delivery device, and the second end of the infusion catheter having an opening through which the infusion drug exits the infusion catheter, the infusion catheter also having one or more placement markers for aligning the second end of the infusion catheter with a distal end of the dialysis catheter;
- a balloon at a distal tip of the infusion catheter, the distal tip being disposed at the second end of the infusion catheter;
- a balloon inflation device configured to selectively inflate and deflate the balloon;
- a tube connecting the balloon and the balloon inflation device to conduct air or fluid to the balloon from the balloon inflation device; and
- a valve attached to the infusion catheter,
- wherein one of the one or more placement markers is configured to be disposed at a proximal end of the valve in order to confirm a preferred placement of the infusion catheter with respect to the dialysis catheter.

19. The dialysis catheter clearance device according to claim 18, wherein the valve has a Luer lock connector and an anti-leak valve, wherein the Luer lock connector is configured to attach to an aspiration port of the dialysis catheter, and wherein the anti-leak valve is configured to seal an outer portion of the infusion catheter and prevent a flow of the infusion drug from escaping, thus directing the infusion drug to the clot.

* * * * *